(12) United States Patent
Carrick et al.

(10) Patent No.: US 7,831,417 B2
(45) Date of Patent: Nov. 9, 2010

(54) PARAMETRIC CALIBRATION METHOD

(75) Inventors: James M. Carrick, San Diego, CA (US); Mark R. Kennedy, South Burlington, VT (US); Jeffrey D. Chismar, San Diego, CA (US)

(73) Assignee: Gen-Probe Incorporated, San Diego, CA (US)

(*) Notice: Subject to any disclaimer, the term of this patent is extended or adjusted under 35 U.S.C. 154(b) by 1010 days.

(21) Appl. No.: 11/599,940

(22) Filed: Nov. 14, 2006

(65) Prior Publication Data

US 2007/0111246 A1    May 17, 2007

Related U.S. Application Data

(60) Provisional application No. 60/737,334, filed on Nov. 14, 2005.

(51) Int. Cl.
*G06F 17/10* (2006.01)
(52) U.S. Cl. .................. 703/2; 702/19; 702/23; 703/11; 435/6; 435/91.2
(58) Field of Classification Search ............ None
See application file for complete search history.

(56) References Cited

U.S. PATENT DOCUMENTS

| 5,219,727 | A | 6/1993 | Wang et al. |
| 6,066,458 | A | 5/2000 | Haaland et al. |
| 6,783,934 | B1 | 8/2004 | McMillan et al. |
| 2003/0104438 | A1 | 6/2003 | Eyre et al. |
| 2003/0165832 | A1 | 9/2003 | Sagner et al. |
| 2005/0118620 | A1 | 6/2005 | Vess |
| 2005/0130211 | A1 | 6/2005 | Shain et al. |

FOREIGN PATENT DOCUMENTS

| EP | 0 525 882 A1 | 2/1993 |
| EP | 0 959 140 A2 | 11/1999 |
| EP | 1 138 784 A2 | 4/2001 |
| EP | 1 158 935 A1 | 3/2005 |
| WO | 2005/030990 A1 | 4/2005 |

OTHER PUBLICATIONS

Orlando et al., "Developments in Quantitative PCR," Clin. Chem. Lab. Med., 1998, 36(5):255-269, Walter de Gruyter, Germany.
Patterson et al., "Increased precision of microbial RNA quantification using NASBA with an internal control," J. Microbiol. Meth., 2005, 60:343-352, Elsevier Biomedical, The Netherlands.
Weusten et al., "Principles of quantitation of viral loads using nucleic acid sequence-based amplification i combination with homogeneous detection using molecular beacons," Nucl. Acids Res., 2002, 30(6) pp. 1-7, Oxford University Press, U.K.
Wilhelm et al., "Validation of an algorithm for automatic quantification of nucleic acid copy numbers by real-time polymerase chain reaction," Analytical Biochem., 2003, 213-225, Elsevier Science, USA.

*Primary Examiner*—Carolyn L. Smith
(74) *Attorney, Agent, or Firm*—Michael J. Gilly

(57) ABSTRACT

Method of preparing a calibration curve and determining the amount of an analyte polynucleotide present in a test sample, particularly using real-time amplification data. The method involves determining indicia of amplification for both the internal calibrator and analyte polynucleotide standards, each as a function of the amount of analyte polynucleotide standard input into the amplification reaction.

33 Claims, 6 Drawing Sheets

US 7,831,417 B2

PARAMETRIC CALIBRATION METHOD

RELATED APPLICATION

This application claims the benefit of U.S. Provisional Application No. 60/737,334, filed Nov. 14, 2005. The entire disclosure of this prior application is hereby incorporated by reference.

FIELD OF THE INVENTION

The present invention relates to the field of biotechnology. More specifically, the invention relates to quantitation of analyte polynucleotides using nucleic acid amplification technology, and still more specifically relates to the use of internal calibrators that coamplify with analyte polynucleotides.

BACKGROUND OF THE INVENTION

Methods involving the kinetic analysis of in vitro nucleic acid amplification have become important tools for quantifying analyte polynucleotides. In these procedures, sometimes referred to as "real-time" amplification procedures, the amount of amplicon present in a nucleic acid amplification reaction mixture is monitored as a function of time over the course of the amplification procedure. Fully automated real-time nucleic acid assays require machine executable algorithms capable of analyzing the time-dependent data acquired during the reaction. In this regard, there is a requirement for data processing algorithms that accurately output an amount or concentration of a nucleic acid that would give rise to an observed amplification result.

Difficulties associated with quantifying the absolute amount of a specific nucleic acid target have been appreciated in the patent literature. These difficulties have been attributed to the exponential nature of the amplification process, and the fact that small differences in any of the variables which control the reaction rate, including the length and nucleotide sequence of the primer pairs, can lead to dramatic differences in amplicon yield. Wang et al., in U.S. Pat. No. 5,219,727 described the use of an internal standard that amplified using the same primers that amplified the analyte polynucleotide, and addressed the fact that use of an unrelated cDNA as a standard necessitated a second set of oligonucleotide primers unrelated to the specific target nucleic acid being quantified. According to Wang et al., analyses which use two sets of unrelated primers can only provide a relative comparison of two independent amplification reactions rather than an absolute measure of a nucleic acid target concentration. Others have followed this teaching and employed internal standards that resemble the target of interest by having similar sequences, and by amplifying with a common pair of primers (see published U.S. patent application Ser. No. 10/230,489). Still others have described quantitative methods that rely on determining the efficiency of amplification (see published European Patent Application EP 1138784). Yet another approach has involved determining amplification ratios for control and target sequences (see U.S. Pat. No. 6,066,458).

Notably, some prior quantitative algorithms that adjust for the efficiency of a coamplified species rely on rationally designed equations to estimate the behavior of a calibration curve over a critical range. As a result, these approaches may not fit the experimental data over the full range of standards employed in a procedure. Alternatively, the prior algorithms are best suited to a particular amplification method, and so are not generally suitable across different assay platforms.

The invention described herein addresses these deficiencies, and has been shown to improve quantitation of analyte polynucleotides.

SUMMARY OF THE INVENTION

A first aspect of the invention relates to a method of preparing a parametric calibration curve for quantifying an analyte polynucleotide contained in a test sample. In accordance with the method, first there is a step for forming a plurality of standard samples, each containing a constant quantity of a nucleic acid calibrator and a known starting quantity of an analyte polynucleotide standard. Next, there is a step for coamplifying the nucleic acid calibrator and the analyte polynucleotide standard in an in vitro nucleic acid amplification reaction for each of the plurality of standard samples. Next, there is a step for determining indicia of amplification for the nucleic acid calibrator and the analyte polynucleotide standard that coamplified in each in vitro nucleic acid amplification reaction of the coamplifying step. This results in a collection of determined indicia of amplification for the nucleic acid calibrator as a function of the known starting quantity of the analyte polynucleotide standard, and a collection of determined indicia of amplification for the analyte polynucleotide standard as a function of the known starting quantity of the analyte polynucleotide standard. Next, there is a step for optimizing a first parametric equation to fit a first curve to the collection of determined indicia of amplification for the nucleic acid calibrator as a function of the known starting quantity of the analyte polynucleotide standard, thereby resulting in a first fitted equation. Next, there is a step for optimizing a second parametric equation to fit a second curve to the collection of determined indicia of amplification for the analyte polynucleotide standard as a function of the known starting quantity of the analyte polynucleotide standard, thereby resulting in a second fitted equation. Next, there is a step for solving the first and second fitted equations at incremental values of the known starting quantity of the analyte polynucleotide standard to result in (a) fitted indicia of amplification for the nucleic acid calibrator as a function of the known starting quantity of the analyte polynucleotide standard, and (b) fitted indicia of amplification for the analyte polynucleotide standard as a function of the known starting quantity of the analyte polynucleotide standard. Finally, there is a step for preparing a three-dimensional parametric calibration curve by relating: (a) fitted indicia of amplification for the analyte polynucleotide standard as a function of the known starting quantity of the analyte polynucleotide standard in a first dimension; (b) fitted indicia of amplification for the nucleic acid calibrator as a function of the known starting quantity of the analyte polynucleotide standard in a second dimension; and (c) a function of the known starting quantity of the analyte polynucleotide standard in a third dimension. In a preferred embodiment, the invented method further includes a step for projecting the three-dimensional parametric calibration curve onto a measurement plane defined by the first and second dimensions, whereby there is created a two-dimensional calibration curve projection in the measurement plane. When this is the case, the coamplifying step can include a procedure for amplifying the nucleic acid calibrator using a first set of amplification oligonucleotides, and amplifying the analyte polynucleotide standard using a second set of amplification oligonucleotides. In this instance, the first and second sets of amplification oligonucleotides preferably are different from each other. Alternatively, the step for determining indicia of amplification can involve determining threshold-based indicia of amplification. Under another alternative, the step for determining indicia of amplification does not involve determining threshold-based indicia of amplification. Under still another alternative, each of the first and second fitted equations has four coefficients. In another preferred embodiment of the invented method, the in vitro nucleic acid amplification reaction in the coamplifying step is an isothermal in vitro nucleic acid amplification reaction. For example, the isothermal in vitro nucleic acid amplification reaction can be a transcription-associated amplification reaction. In a different preferred embodiment, when the invented method includes the step for projecting the three-dimensional parametric calibration curve onto the measurement plane there are further included steps for (a) forming a test reaction mixture that includes the test sample and the constant quantity of the nucleic acid calibrator, (b) coamplifying in an in vitro nucleic acid test amplification reaction the nucleic acid calibrator and any analyte polynucleotide contained in the test reaction mixture, and (c) determining indicia of amplification for the nucleic acid calibrator and the analyte polynucleotide that coamplified in the in vitro nucleic acid test amplification reaction. More preferably, there is an additional step for quantifying the analyte polynucleotide contained in the test sample. Still more preferably, the quantifying step involves comparing the determined indicia of amplification for the nucleic acid calibrator and the analyte polynucleotide that coamplified in the in vitro nucleic acid test amplification reaction with the two-dimensional calibration curve projection in the measurement plane. Alternatively, the quantifying step can involve first specifying in the measurement plane a test sample data point having coordinates for the determined indicia of amplification for the nucleic acid calibrator and the analyte polynucleotide that coamplified in the in vitro nucleic acid test amplification reaction, and then determining a value for a third dimension coordinate of the three-dimensional parametric calibration curve that minimizes the distance separating the test sample data point and a point on the two-dimensional calibration curve projection in the measurement plane. When this is the case, the step for determining the value for the third dimension coordinate of the three-dimensional parametric calibration curve can involve calculating the length of a right triangle hypotenuse. Alternatively, the coamplifying step can involve amplifying the nucleic acid calibrator using a first set of amplification oligonucleotides, and amplifying the analyte polynucleotide standard using a second set of amplification oligonucleotides, where the first and second sets of amplification oligonucleotides are different from each other. Under still another alternative, the step for determining indicia of amplification involves determining threshold-based indicia of amplification. Under yet another alternative, the step for determining indicia of amplification does not involve determining threshold-based indicia of amplification. Under still yet another alternative, each of the first and second fitted equations has four coefficients. Under another alternative, the in vitro nucleic acid amplification reaction in the coamplifying step is an isothermal in vitro nucleic acid amplification reaction. Under another alternative, the isothermal in vitro nucleic acid amplification reaction is a transcription-associated amplification reaction.

Another aspect of the invention relates to a method of quantifying an analyte nucleic acid contained in a test sample by internal calibration adjustment of nucleic acid amplification results. The method includes a first step for collecting a standard data set and a test data set. The standard data set includes results from a plurality of standard nucleic acid amplification reactions, where each standard nucleic acid amplification reaction includes a constant starting quantity of a nucleic acid calibrator and a different known starting quantity of an analyte polynucleotide standard. The plurality of standard nucleic acid amplification reactions yield indicia of amplification for the analyte polynucleotide standard as a function of the known starting quantity of the analyte polynucleotide standard, and indicia of amplification for the nucleic acid calibrator that coamplified with the analyte polynucleotide standard as a function of the known starting quantity of the analyte polynucleotide standard. The test data set includes results from a test nucleic acid amplification reaction that includes the constant starting quantity of the nucleic acid calibrator and an unknown starting quantity of the analyte nucleic acid. The test nucleic acid amplification reaction yields an indicium of amplification for the analyte nucleic acid contained in the test sample, and an indicium of amplification for the nucleic acid calibrator that coamplified with the analyte nucleic acid. Next, there is a step for preparing a three-dimensional parametric calibration curve that includes: (a) a first dimension that includes solutions to a first optimized parametric equation that expresses indicia of amplification for the analyte polynucleotide standard as a function of the known starting quantity of the analyte polynucleotide standard; (b) a second dimension that includes solutions to a second optimized parametric equation that expresses indicia of amplification for the nucleic acid calibrator as a function of the known starting quantity of analyte polynucleotide standard; and (c) a third dimension parameter of the first and second optimized parametric equations. This third dimension parameter is a function of the known starting quantity of analyte polynucleotide standard used in the plurality of standard nucleic acid amplification reactions. Notably, the first and second dimensions of the three-dimensional parametric calibration curve define a measurement plane. This measurement plane includes a projection of the three-dimensional parametric calibration curve. Next, there is a step for specifying a test sample data point in the measurement plane, wherein the test sample data point includes a set of coordinates for the indicium of amplification for the analyte nucleic acid and the indicium of amplification for the nucleic acid calibrator that coamplified with the analyte nucleic acid in the test nucleic acid amplification reaction. Finally, there is a step for determining the minimum distance between the test sample data point specified in the measurement plane and the projection of the three-dimensional parametric calibration curve in the measurement plane by varying the value of the third dimension parameter. The value of the third dimension parameter which results in the determined minimum distance estimates the quantity of the analyte nucleic acid contained in the test sample. In accordance with a first generally preferred embodiment, the determining step involves determining by an iterative computing process. When this is the case, it is desirable for the iterative computing process to involve calculating the hypotenuse length for a plurality of right triangles. More preferably, the plurality of standard nucleic acid amplification reactions and the test nucleic acid amplification reaction are isothermal amplification reactions that do not use thermal cycling to synthesize amplicons. In an alternative preferred embodiment, the plurality of standard nucleic acid amplification reactions and the test nucleic acid amplification reaction amplify the analyte nucleic acid and analyte polynucleotide standard using a first set of two amplification oligonucleotides, and amplify the nucleic acid calibrator using a second set of two amplification oligonucleotides. In this instance, the first and second sets of amplification oligonucleotides are identical to each other. In another alternative preferred embodiment, the plurality of standard nucleic acid amplification reactions and the test nucleic acid amplification reaction amplify the analyte nucleic acid and analyte polynucleotide standard using a first set of two amplification oligonucleotides, and amplify the nucleic acid calibrator using a second set of two amplification oligonucleotides. In this instance, the first and second sets of amplification oligonucleotides are not identical to each other. In still another alternative preferred embodiment, the collecting step, the preparing step, the specifying step, and the determining step are each automated by computer software that is an integral component of a device used for performing the test nucleic acid amplification reaction and the plurality of standard nucleic acid amplification reactions. In accordance with another generally preferred embodiment, each of the plurality of standard nucleic acid amplification reactions and the test nucleic acid amplification reaction can be isothermal amplification reactions that do not use thermal cycling to synthesize amplicons. In accordance with another generally preferred embodiment, the plurality of standard nucleic acid amplification reactions and the test nucleic acid amplification reaction can amplify the analyte nucleic acid and analyte polynucleotide standard using a first set of two amplification oligonucleotides, and amplify the nucleic acid calibrator using a second set of two amplification oligonucleotides. In this instance the first and second sets of amplification oligonucleotides are identical to each other. In accordance with another generally preferred embodiment, the plurality of standard nucleic acid amplification reactions and the test nucleic acid amplification reaction amplify the analyte nucleic acid and analyte polynucleotide standard using a first set of two amplification oligonucleotides, and amplify the nucleic acid calibrator using a second set of two amplification oligonucleotides. In this instance the first and second sets of amplification oligonucleotides are not identical to each other. In accordance with yet another generally preferred embodiment, the first and second optimized parametric equations each have four fixed coefficients.

Another aspect of the invention relates to a system for quantifying an initial amount of an analyte polynucleotide contained in a test sample. Generally speaking, this system includes as key components: (1) an obtaining means, (2) a programmable processing means, and (3) a reporting means. With specific reference to the first of these components, there is a means for obtaining (a) a standard data set of time-dependent indicia of amplification for each of an analyte polynucleotide standard and a nucleic acid calibrator that coamplified therewith in a plurality of in vitro nucleic acid standard amplification reactions carried out using a range of starting amounts of analyte polynucleotide standard and a constant starting amount of nucleic acid calibrator, and (b) a test data set of time-dependent indicia of amplification for each of the analyte polynucleotide contained in the test sample and a nucleic acid calibrator that coamplified therewith in an in vitro nucleic acid test amplification reaction. With specific reference to the second component of the system invention, there is a programmable means for processing the standard data set and the test data set by comparing the test data set with a three-dimensional calibration curve prepared from the standard data set. The three-dimensional calibration curve includes a first dimension that includes solutions to a first optimized parametric equation that expresses indicia of amplification for analyte polynucleotide standard as a function of the known starting quantities of analyte polynucleotide standard input into the in vitro nucleic acid standard amplification reactions. The three-dimensional calibration curve further includes a second dimension that includes solutions to a second optimized parametric equation that expresses indicia of amplification for coamplified nucleic acid calibrator as a function of the known starting quantities of analyte polynucleotide standard input into the in vitro nucleic acid standard amplification reactions. The three-dimensional calibration curve further includes a third dimension parameter of the first and second optimized parametric equations. This third dimension parameter includes the known starting quantities of analyte polynucleotide standard input into the in vitro nucleic acid standard amplification reactions. Notably, the first and second dimensions of the three-dimensional parametric calibration curve define a measurement plane, and this measurement plane includes a projection of the three-dimensional parametric calibration curve. With specific reference to the third component of the invented system, there is a means for reporting a result obtained from the processed test data set that quantifies the initial amount of analyte polynucleotide contained in the test sample.

BRIEF DESCRIPTION OF THE DRAWINGS

FIG. 6A shows a parametric calibration curve and a test sample data point having coordinates (Tt?,ICt?). FIG. 6B shows how the distance between the test sample data point and different points on the two-dimensional calibration curve in the measurement plane can be calculated. Two arbitrary points on the calibration curve are identified by $(Tt(S)_1, ICt(S)_1)$ and $(Tt(S)_2, ICt(S)_2)$. The distance separating the test sample data point and the calibration curve can be determined by calculating the hypotenuse ($\delta$) of a right triangle.

DEFINITIONS

Figure 1:
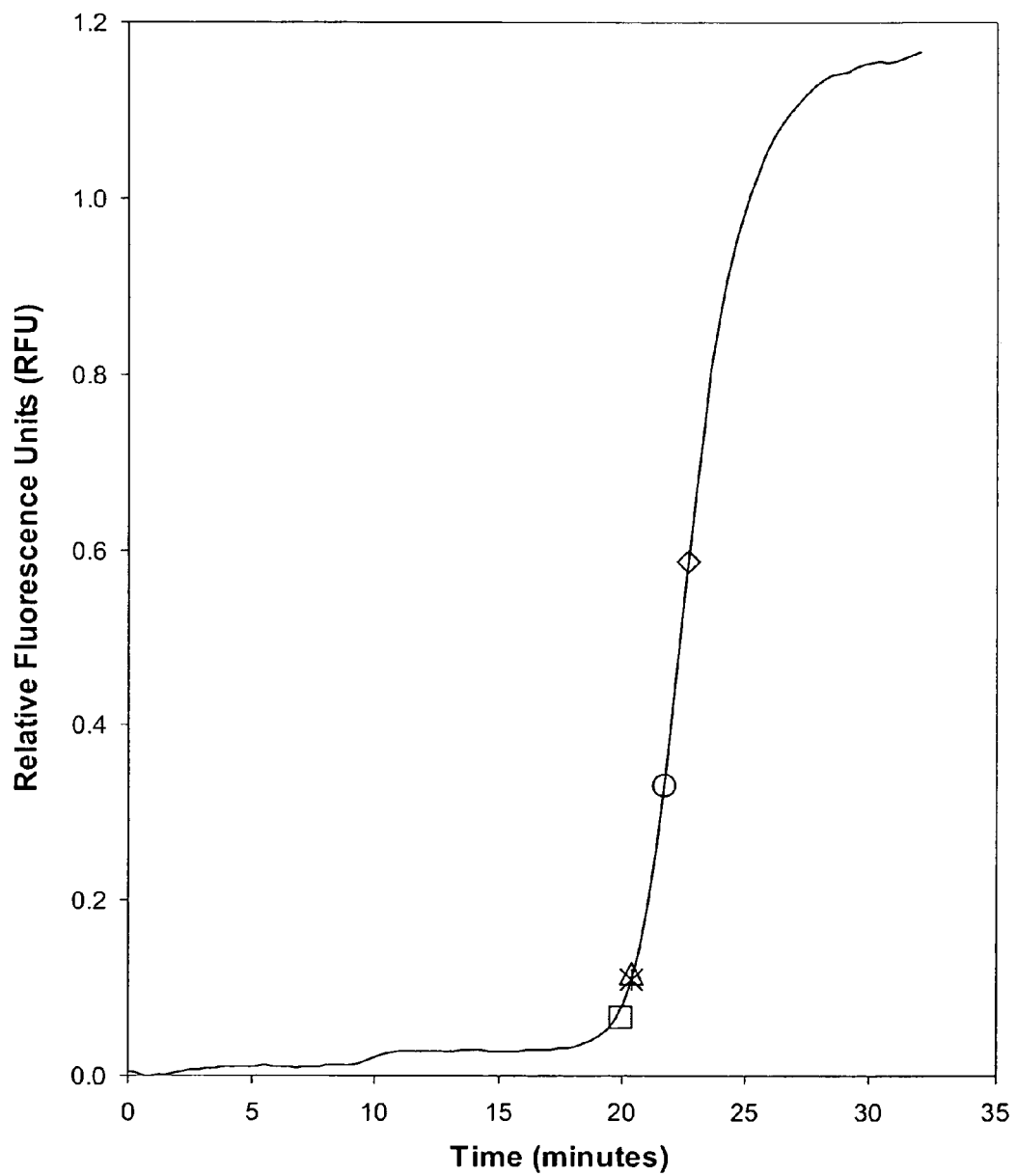
FIG. 1 is a graphic presentation of an exemplary real-time run curve showing the positions corresponding to different indicia of amplification. Symbols on the run curve identify indicia of amplification for TArc (□), OTArc (Δ), TTime (x), the maximum of the first derivative (◇), and the maximum of the second derivative (○). Notably, the determined OTArc and TTime indicia of amplification are nearly coincident.

The following terms have the following meanings for the purpose of this disclosure, unless expressly stated to the contrary herein.

As used herein, "polynucleotide" means either RNA, DNA, or a chimeric molecule containing both RNA and DNA.

By "analyte polynucleotide" or "analyte nucleic acid" is meant a polynucleotide of interest that is to be quantified.

As used herein, a "test sample" is any sample to be investigated for the presence of a particular polynucleotide species. Test samples include any tissue or polynucleotide-containing material obtained from a human, animal, environmental, or laboratory-derived or synthetic sample.

As used herein, "standard samples" are samples containing an analyte polynucleotide standard.

By "analyte polynucleotide standard" is meant a known quantity of an analyte polynucleotide, or fragment thereof. For example, an HIV-1 analyte polynucleotide standard may contain a known number of copies of an HIV-1 genome, HIV-1 transcript, or in vitro synthesized transcript representing a portion of the viral genome.

An "amplicon" is a polynucleotide product of an amplification reaction wherein a target nucleic acid sequence served as the template for synthesis of polynucleotide copies or amplification products.

By "amplification" or "nucleic acid amplification" or "in vitro nucleic acid amplification" is meant any known procedure for obtaining multiple copies, allowing for RNA and DNA equivalents, of a target nucleic acid sequence or its complement or fragments thereof. Amplification of "fragments thereof" refers to production of an amplified nucleic acid containing less than the complete target region nucleic acid sequence or its complement. Such fragments may be produced by amplifying a portion of the target nucleic acid, for example, by using an amplification oligonucleotide which hybridizes to, and initiates polymerization from, an internal position of the target nucleic acid.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target nucleic acid" or "target" is meant a nucleic acid containing a target nucleic acid sequence. In general, a target nucleic acid sequence that is to be amplified will be positioned between two oppositely disposed oligonucleotides, and will include the portion of the target nucleic acid that is complementary to each of the oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription-associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target nucleic acid. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. patent application having Ser. No. 11/213,519 are particularly embraced by the definition and are highly preferred for use in connection with the method disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

By "amplification oligonucleotide" or "amplification oligomer" is meant an oligomer that hybridizes to a target nucleic acid, or its complement, and participates in a nucleic acid amplification reaction. Examples of amplification oligomers include primers that contain a 3' end that is extended as part of the amplification process, but also include oligomers that are not extended by a polymerase (e.g., a 3' blocked oligomer) but may participate in, or facilitate efficient amplification from a primer. Preferred size ranges for amplification oligomers include those that are about 10 to about 60 nt long and contain at least about 10 contiguous bases, and more preferably at least 12 contiguous bases that are complementary to a region of the target nucleic acid sequence (or a complementary strand thereof). The contiguous bases are preferably at least about 80%, more preferably at least about 90%, and most preferably about 100% complementary to the target sequence to which amplification oligomer binds. An amplification oligomer may optionally include modified nucleotides or analogs, or additional nucleotides that participate in an amplification reaction but are not complementary to or contained in the target nucleic acid. An amplification oligomer that is 3' blocked but capable of hybridizing to a target nucleic acid and providing an upstream promoter sequence that serves to initiate transcription is referred to as a "promoter provider" oligomer.

A "primer" is an amplification oligomer that hybridizes to a template nucleic acid and has a 3' OH end that can be extended by a DNA polymerase. The 5' region of the primer may be non-complementary to the target nucleic acid (e.g., a promoter sequence), resulting in an oligomer referred to as a "promoter-primer." Those skilled in the art will appreciate that any oligomer that can function as a primer can be modified to include a 5' promoter sequence, and thus could function as a promoter-primer. Similarly, any promoter-primer can be modified by removal of, or synthesis without, a promoter sequence and still function as a primer.

As used herein, a "set" of amplification oligonucleotides refers to a collection of two or more amplification oligonucleotides that cooperatively participate in an in vitro nucleic acid amplification reaction to synthesize amplicons.

As used herein, a "probe" is an oligonucleotide that hybridizes specifically to a target sequence in a nucleic acid, preferably in an amplified nucleic acid, under conditions that promote hybridization, to form a detectable hybrid.

As used herein, "time-dependent" monitoring of nucleic acid amplification, or monitoring of nucleic acid amplification in "real-time" refers to a process wherein the amount of amplicon present in a nucleic acid amplification reaction is measured as a function of reaction time or cycle number and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement (y-axis). Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation generally is substantially lower than the rate of amplicon production in the log-linear phase, and may even approach zero.

As used herein, the phrase "indicia of amplification" refers to features of real-time run curves which indicate a predetermined level of progress in nucleic acid amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

By "nucleic acid calibrator" or "internal calibrator" is meant a polynucleotide that is capable of amplification in an in vitro nucleic acid amplification reaction, and that is distinguishable from an analyte polynucleotide coamplified in the same amplification reaction. In certain preferred embodiments, the internal calibrator and the analyte polynucleotide are coamplified in an in vitro nucleic acid amplification reaction using one or more different amplification oligomers or primers. For example, the analyte and internal calibrator polynucleotides employed in the working Examples detailed below were amplified using amplification oligonucleotides that were not shared. In other preferred embodiments, the internal calibrator and the analyte polynucleotide are coamplified in an in vitro nucleic acid amplification reaction using identical amplification oligomers or primers.

As used herein, "internal calibration adjustment" refers to a quantitative procedure for determining the starting amount of analyte nucleic acid in a test sample that underwent amplification by comparison with results obtained for a coamplified target nucleic acid referred to as a "nucleic acid calibrator" or "internal calibrator."

By "parametric equation" is meant an equation that allows variables, called "parameters" or independent variables, to be filled-in with any specified value to obtain the values of dependent variables. For example, if a two-dimensional curve is traced out as a function of a third variable S, then the position along the curve at any value of S can be described by parametric equations: $x=x(S)$ and $y=y(S)$. Then x and y are related to each other through their dependence on the "parameter" S.

As used herein, a "parameter" is the independent variable in a set of parametric equations.

As used herein, a "parametric calibration curve" is a mathematical relationship, including visual displays and electronic representations thereof, between (a) indicia of amplification for known amounts of analyte polynucleotide standard as a function of the parameter representing the known starting quantity of analyte polynucleotide standard present in a reaction mixture at the time an amplification reaction was initiated (i.e., "Tt(S)"), and (b) indicia of amplification for a known, constant amount of nucleic acid calibrator that coamplified with the analyte polynucleotide standard in the same amplification reaction as a function of the parameter representing the known starting quantity of analyte polynucleotide standard present in the reaction mixture at the time the amplification reaction was initiated (i.e., "ICt(S)"). For example, a three-dimensional parametric calibration curve may display, or relate in electronic spreadsheet format, Tt(S) in one dimension, ICt(S) in another dimension, and the known starting quantity of analyte polynucleotide standard present in a reaction mixture at the time the amplification reaction was initiated (i.e., "S") in a third dimension. A projection of this three-dimensional calibration curve onto the two-dimensional measurement plane represents a two-dimensional parametric calibration curve.

As used herein, a "parametric calibration method" is a quantitative method involving the preparation and/or use of a parametric calibration curve.

As used herein, the phrase "as a function of" describes the relationship between a dependent variable (i.e., a variable that depends on one or more other variables) and an independent variable (i.e., a variable that may have its value freely chosen without considering the values of any other variables), wherein each input value for the independent variable relates to exactly one output value for the dependent variable.

As used herein, "optimizing" a parametric equation refers to a process, as commonly practiced in mathematical modeling or curve fitting procedures, for obtaining numerical values for coefficients in a parametric equation to yield an expression that "fits" or approximates experimental measurements.

As used herein, the terms "optimized parametric equation," and "fitted equation" and "fitted parametric equation" are alternative references to a parametric equation containing fixed numerical values for coefficients as the result of an optimizing procedure.

As used herein, "incremental" values refer to values that increase or decrease gradually by regular degrees.

As used herein, an "iterative" computing method attempts to solve a problem (e.g., an equation or system of equations) by successive approximations to the solution.

As used herein, the phrase "threshold-based indicia of amplification" refers to indicia of amplification that require quantifying a baseline signal for amplicon synthesis, and that further require a calculation (such as calculation of a difference or a quotient) based on this quantified baseline signal. TTime determinations are examples of threshold-based indicia of amplification, while TArc and OTArc determinations are examples of non-threshold-based indicia of amplification.

As used herein, "specifying" in a plane (e.g., specifying a data point in a measurement plane) refers to a procedure, which may involve use of computer software, for designating a point in the plane of a two-dimensional graph. This can involve identifying coordinates (e.g., x and y coordinates) for the data point in the plane.

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

DETAILED DESCRIPTION OF THE INVENTION

Herein there are disclosed methods for improving the quantitation of analyte polynucleotides using real-time nucleic acid amplification. More specifically, the invention relates to methods for assessing internal calibration results in real-time amplification assays, and to adjustments in the quantitation of an analyte polynucleotide that take into account the internal calibration results, thereby improving assay precision and accuracy. These methods allow for correction of sample-to-sample variability where target amounts are identical, but amplification conditions differ slightly. Using a space curve parametric calibration, measured indicia from the amplification profiles of both an analyte polynucleotide and an internal calibrator are used to estimate the analyte polynucleotide copy number present in an unknown test sample.

In accordance with certain embodiments of the disclosed method, results from real-time amplification reactions are processed to calculate indicia of amplification. Generally speaking, these indicia are indicators of the extent of an amplification reaction. The measured or calculated indicia of amplification can then be used to generate two different two-dimensional plots—one for an analyte polynucleotide standard and another for an internal calibrator. More specifically, the measured indicia of amplification for these targets are plotted against some measure of the number of copies of analyte polynucleotide standard input into the amplification reaction. Information from these plots can then be combined to create a calibration space curve, such as a three-dimensional calibration curve. The data sets used in these procedures are generated from a collection of amplification reactions, each containing a known number of copies of an analyte polynucleotide standard, and each containing a constant number of internal calibrator templates prior to initiating the amplification reaction.

The variables (i.e., "coefficients") of a model parametric equation can be fitted to the data points for each of the two-dimensional plots to result in two equations that define curves fitting the measured values. More specifically, the coefficients of a preselected parametric equation can be optimized or determined by fitting the model equation to the measured data points. This can be accomplished by solving for numerical values of the coefficients that minimize differences between measured data and model (i.e., fitted) values, thereby resulting in a fitted curve. Those having an ordinary level of skill in the art will recognize that these procedures can be carried out using curve-fitting techniques. One of the resulting equations expresses the measurable indicia of amplification for known quantities of the analyte polynucleotide standard (Tt) as a first function of the known number of analyte polynucleotide standard molecules (S) input into the reaction (i.e., $Tt=Tt(S)$). The second equation expresses the measurable indicia of amplification for the internal calibrator (ICt) as a second function of the known number of analyte polynucleotide standard molecules input into the reaction (i.e., $ICt=ICt(S)$). In this manner Tt and ICt are related to each other through their dependence on the parameter S. A third equation expresses the number of analyte polynucleotide molecules input into the amplification reaction (Z) as a function of the known number of analyte polynucleotide standard molecules input into the reaction (i.e., $Z=Z(S)$). For example, in certain specific embodiments this third function may take the form $Z=\log_{10}(S)$.

The calibration relationships can be plotted as a parametric curve in the measurement plane with each data point having coordinates (Tt, ICt), where the number of analyte polynucleotide standard molecules (S) is the parameter of the curve in the measurement plane. Alternatively, the calibration relationship can be plotted as a space-curve in three dimensions where the parameter S is plotted as the height above the measurement plane. The indicia of amplification for the analyte polynucleotide and internal calibrator amplified in a test reaction containing an unknown number of analyte polynucleotide molecules can also be plotted in the measurement plane of the parametric calibration plot.

Figure 5:
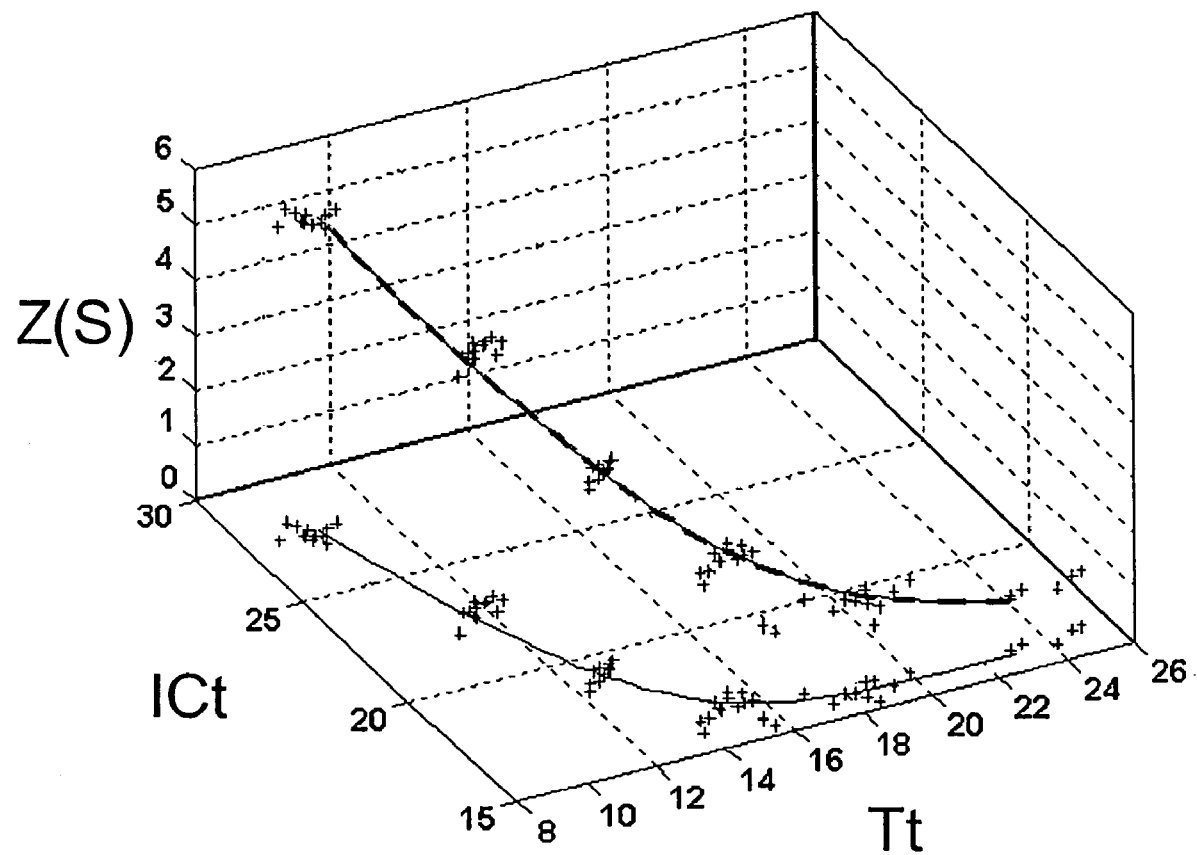
FIG. 5 is a three-dimensional graph illustrating the relationship between the indicia of amplification for the analyte polynucleotide standard (Tt(S)) expressed in TTime units (i.e., minutes); the indicia of amplification for the internal calibrator (ICt(S)) expressed in TTime units (i.e., minutes), and a function of the amount of analyte polynucleotide standard input into an amplification reaction, expressed as $Z(S) = \log_{10}(S)$. Data points representing determinations of the indicia of amplification for individual amplification reactions are indicated by plus signs (+). The dashed heavy curve represents the three-dimensional parametric calibration curve. The solid curve represents the parametric calibration curve plotted in the measurement plane. The curve in the measurement plane is the projection of the three-dimensional curve onto the measurement plane.
Figure 6A:
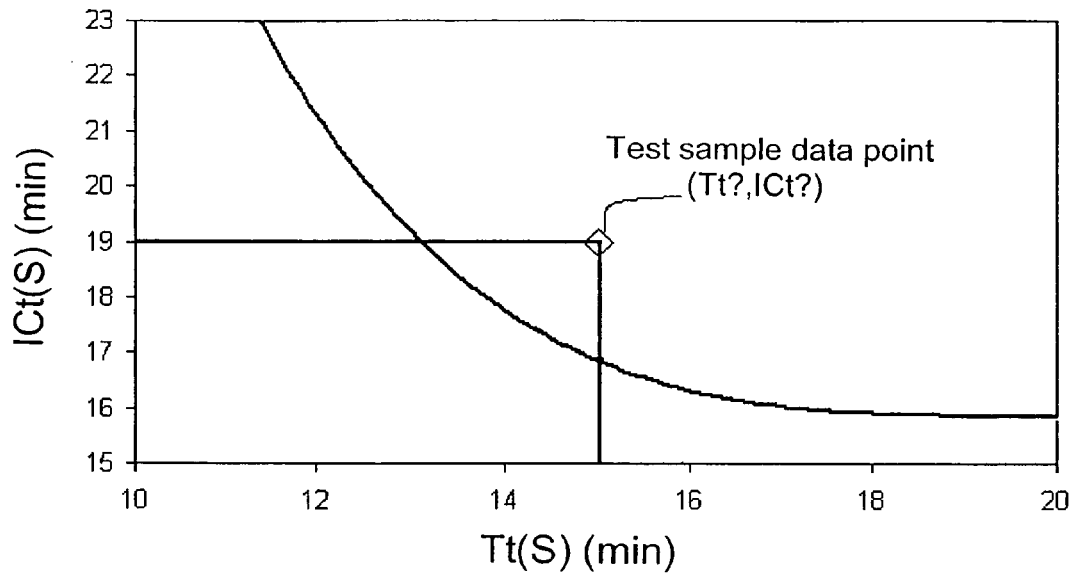
FIGS. 6A-6B are graphs illustrating a parametric calibration curve and a test sample data point plotted in the measurement plane.

FIG. 6A illustrates a two-dimensional relationship corresponding to the projection onto the measurement plane of a three-dimensional parametric calibration curve, such as that shown in FIG. 5. Also shown is a test sample data point, indicated by (Tt?,ICt?), representing the indicia of amplification coordinates for analyte and internal calibrator polynucleotides in an amplification reaction initiated with an unknown number of analyte polynucleotide molecules. This test sample amplification reaction also included the same constant amount of internal calibrator employed in all of the standard reactions used for creating the calibration curves. As discussed above, there are at least two methods for producing the two-dimensional relationship shown in the figure. Of course, since $Z=Z(S)$, the z-axis is assumed in the graphs presented in FIGS. 6A-6B. Thus, FIG. 6A illustrates specification in the measurement plane of a parametric calibration curve relating the coordinates of the indicia of amplification measured for the coamplified analyte polynucleotide and internal calibrator in a test reaction.

To estimate the starting analyte polynucleotide copy number used in the test reaction, the value of S on the parametric calibration curve in the measurement plane is varied to locate the point on the calibration curve in the measurement plane that is nearest to the test sample coordinates in the measurement space. The distance between the coordinate for the test sample in the measurement space and a point on the model calibration space curve can be calculated simply by using the Euclidean norm and the following equation.

$$\delta^2 = (Tt? - Tt(S))^2 + (ICt? - ICt(S))^2 \quad \text{(Eq 1)}$$

In this equation, the square of the hypotenuse ($\delta$) of a right triangle which defines the distance between the test coordinate in the measurement plane (Tt?, ICt?) and a point on the calibration curve in the measurement plane determined for a particular S value (Tt(S), ICt(S)) equals the square of the difference between the measured indicia of amplification for the unknown analyte polynucleotide and the indicia of amplification for a point on the calibration curve (i.e., $(Tt? - Tt(S))^2$) added to the square of the difference between the measured indicia of amplification for the internal calibrator in the test reaction and the indicia of amplification for a point on the calibration curve (i.e., $(ICt? - ICt(S))^2$). The analyte polynucleotide copy number value (i.e., the value of S in the z-dimension) on the parametric calibration curve corresponding to that value of S which gives the minimal distance (i.e., minimal $\delta$) between the test sample coordinate in the measurement plane and the calibration curve estimates the analyte polynucleotide copy number in the test sample. Those having an ordinary level of skill in the art will appreciate that determination of the value of S that provides this minimal distance can be accomplished using a reiterative computing process that involves calculating the value of $\delta$ at different values of S.

Figure 6B:
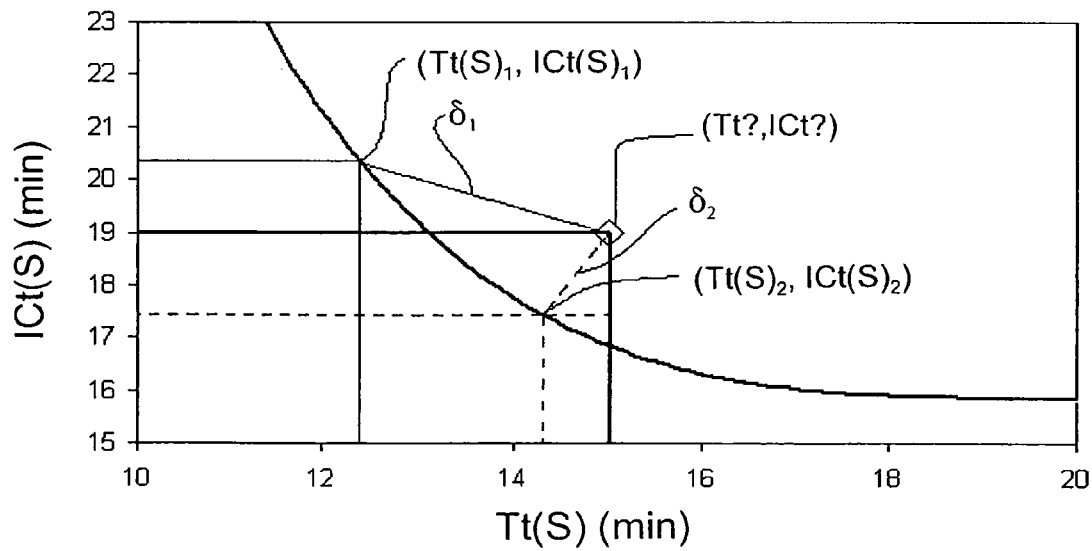

FIG. 6B particularly illustrates this method of estimating the amount of analyte polynucleotide in a test sample that would give rise to the data point having the coordinates (Tt?, ICt?), as shown in FIG. 6A. The method preferably involves varying the value of the parameter S to locate the point on the parametric calibration curve in the measurement plane which is nearest to the test sample data point in the measurement plane. Determining the value of S that minimizes the magnitude of the separation between the data point having the coordinates (Tt?,ICt?) and the parametric calibration curve projection in the measurement plane estimates the amount of analyte polynucleotide contained in the test sample. The magnitude of the separation between the parametric calibration curve in the measurement plane and the point representing the coordinates for the test sample is indicated by the symbol, "$\delta$." FIG. 6B shows two arbitrary points on the parametric calibration curve in relation to the test sample data point. Each point is associated with a unique set of coordinates (Tt(S),ICt(S)). Coordinates for the test sample data point are (Tt?,ICt?). Each of the points identified on the calibration curve in the measurement plane can be used to generate a triangle that is unique for each level of input analyte polynucleotide. In each case the hypotenuse of the triangle represents the magnitude of separation between the test data point and the curve drawn in the measurement plane. The magnitude of the hypotenuse can be calculated simply by applying the Pythagorean theorem, as embodied in Equation (1).

Notably, the present method for analyzing and using results from a coamplifiable internal calibrator differs substantially from previously described methods. For example, the disclosed method applies equally well to data obtained when the analyte polynucleotide and internal calibrator nucleic acids amplify using the same amplification oligonucleotides, or different amplification oligonucleotides. Also, there is no requirement for establishing ratios between measured values determined for standards and internal calibrators. Moreover, the disclosed method generalizes to any form of calibration fitting functions, and it generalizes to larger numbers of independent measurements. For example, if each of the time records of analyte polynucleotide standard and internal calibrator are characterized by two indicia each, the four indicia would form a four-dimensional hyperplane and the calibration curve would be a five-dimensional space curve. Thus, the method disclosed herein is broadly applicable, and its value is not limited to a particular in vitro amplification method.

Useful Amplification Methods

Examples of amplification methods useful in connection with the parametric calibration method include, but are not limited to: Transcription Mediated Amplification (TMA), Single-Primer Nucleic Acid Amplification, Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published U.S. patent application Ser. No. 11/213,519, published European patent application EP 0 525 882, U.S. Pat. No. 4,965,188, U.S. Pat. No. 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform nucleic acid amplification reactions are hereby incorporated by reference.

Amplification reactions that require only a single extendable primer are particularly preferred for use in connection with the disclosed calibration method. These reactions include transcription-associated amplification systems that employ a single extendable primer in combination with a 3'-blocked oligonucleotide that cannot be extended by a nucleic acid polymerase. Methods for carrying out such amplification reactions are, for example, detailed in U.S. patent application Ser. No. 11/213,519.

Examples of Useful Indicia of Amplification

A variety of indicia of amplification can be used in connection with the disclosed method. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720, the disclosure of which is incorporated by reference herein. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934, the disclosure of which is incorporated by reference. Still other useful indicia of amplification include "TTime," "TArc" and "OTArc."

FIG. 1 shows that the above-referenced indicia of amplification identify different points on the same real-time run curve. Nevertheless, each of these different indicia can be used in accordance with the disclosed calibration algorithm to create a calibration curve or plot. This illustrates the versatility of the technique described herein.

Methods of Determining TTime Values

Figure 2:
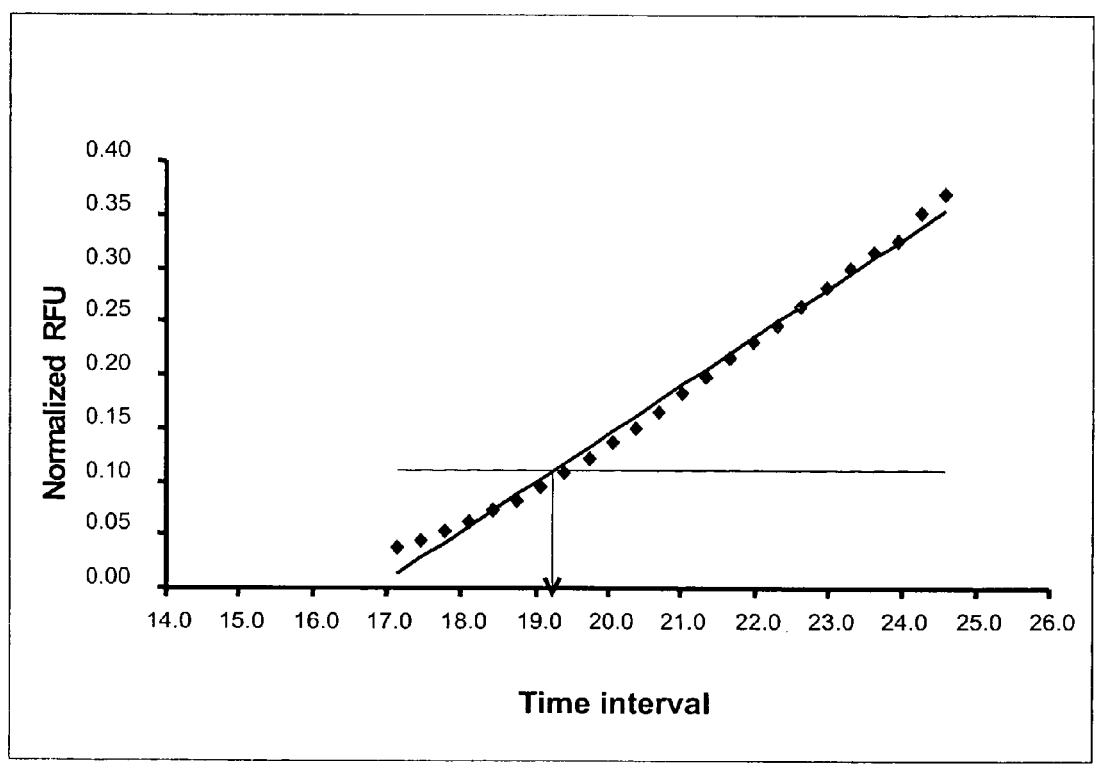
FIG. 2 is graphic illustration of a procedure used for determining a TTime value. The x-axis displays the time interval, and the y-axis displays background-subtracted and normalized RFU (relative fluorescence units). A thin horizontal line indicates a fluorescence threshold. Fluorescence readings as a function of time are indicated by filled diamonds (◆). The heavy line has been drawn to indicate the slope of the data over the interval 0.04-0.36.

Simply stated, TTime values estimate the time at which a particular threshold indicating amplicon production is passed in a real-time amplification reaction. The algorithm for calculating and using TTime values has been described in U.S. patent application Ser. No. 60/659,874, the disclosure of which is incorporated by reference. FIG. 2 illustrates the method of determining a TTime value on a segment of a real-time run curve.

To illustrate the general features of the TTime determination, it will be assumed that data collected as a series of time-based fluorescence readings was obtained, and that such data can be referred to in terms of Relative Fluorescent Units ("RFUs"). Each data point, measured at a given time interval, is referred to as RFU(t). In general, each RFU(t) plot is characterized by an initial, substantially flat portion at or near a minimum level, followed by an abrupt and relatively steeply sloped portion, and ending with a generally flat portion at or near a maximum level.

The TTime (also known as "time-of-emergence") refers to the time at which the data RFU(t), normalized as discussed below, reaches a predefined threshold value. Using standard curves, as will be described in more detail below, the TTime determined for a particular sample can, without adjustment for amplification of an internal calibrator, be correlated with an analyte amount or concentration, thereby indicating the analyte amount or concentration for the sample. In general, the higher the concentration of the analyte of interest, the steeper the RFU(t) curve and the sooner the TTime.

The first step of the TTime determination procedure is background adjustment and normalization of the data. Background adjustment is performed to subtract that portion of the signal data RFU(t) that is due to background "noise" from, for example, stray electromagnetic signals from other modules in the instrument used for conducting and monitoring nucleic acid amplification reactions. Background adjustment is performed by simply subtracting a background value "BG" from the data RFU(t) to obtain adjusted data RFU*(t). That is, RFU*(t)=RFU(t)−BG.

The background BG, is determined as follows. First, determine the time intervals between data points. The time interval is determined by multiplying cycle time (i.e., the time between consecutive data measurements) by the data point (i.e., 0th data point, 1st data point, 2nd data point, ... nth data point) and divide by 60 seconds. For example, assuming a cycle time of 30 seconds, the time interval for the 15th data point is (15×30 sec.)/60 sec.=7.5 minutes. Next, find the midpoint of the signal data by adding the minimum signal data point and the maximum signal data point and dividing by two. That is: $(RFU_{max}+RFU_{min})/2$. Starting at the time corresponding to the midpoint value and working backwards, calculate the slope for each pair of data points:

$(RFU(t)−RFU(t−1))/\Delta t(t \rightarrow t−1)$. Find where the slope of RFU(t) flattens out by finding the first slope value that is less than the static slope value (i.e., the value before the RFU(t) curve begins its upward slope, e.g., −0.0001). Once this slope is found, find the next slope that is not negative; this value is $H_{index}$. Next, take the mean of the entire range of RFU(t) values starting at the first data point and go to the RFU value that corresponds to the $H_{index}$ value. Preferably, the mean of this data is taken using the TRIMMEAN function of an EXCEL spreadsheet (Microsoft Corporation; Redmond, Wash.) on this range of data using a static back trim value of 0.15. This mean value is the background, BG.

To normalize the data, each data point, adjusted for the background, is divided by the maximum data point, also adjusted for the background. This can be calculated as follows.

$$\text{Normalized } RFU = RFU_n(t) \quad \text{(Eq 2)}$$
$$= \frac{RFU^*(t)}{RFU^*_{max}}$$
$$= \frac{RFU(t) - BG}{RFU_{max} - BG}$$

Thus, the $RFU_n(t)$ will be between 0 and 1.

Next, the range of data is calculated by subtracting $RFU_{n(min)}$ from $RFU_{n(max)}$. If the calculated range does not meet or exceed a specified, minimum range (e.g., 0.05), the data is considered suspect and of questionable reliability, and, thus, the TTime will not be calculated. The minimum range is determined empirically and may vary from one fluorescence measuring instrument to the next. Ideally, the specified minimum range is selected to ensure that the variation of data values from minimum to maximum exceeds the noise of the system.

Next, a curve fit procedure is applied to the normalized, background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve which fits the data, is to find the time corresponding to the point at which the curve intersects a predefined threshold value. In the preferred embodiment, the threshold for normalized data is 0.11. The high and low bounds are determined empirically as that range over which curves fit to a variety of control data sets exhibit the least variability in the time associated with the given threshold value. In the preferred embodiment, the low bound is 0.04 and the high bound is 0.36. The curve is fit for data extending from the first data point below the low bound through the first data point past the high bound.

Next, determine whether the slope of the fit is statistically significant. For example, if the p value of the first order coefficient is less than 0.05, the fit is considered significant, and processing continues. If not, processing stops. Alternatively, the validity of the data can be determined by the $R^2$ value.

The slope (m) and intercept (b) of the linear curve are determined for the fitted curve. With that information, TTime can be determined by the following equation.

$$TTime = \frac{\text{Threshold} - b}{m} \quad \text{(Eq 3)}$$

Methods of Determining TArc Values

Time-dependent indicia of amplification referred to as "TArc" and "OTArc" are determined using vector-based analyses of real-time run curves. The TArc value identifies the point in time at which a growth curve begins to curve or "inflect" upward. This determined point can be used for creating a standard curve, or for establishing a parameter of an amplification reaction that relates to the amount or concentration of an analyte polynucleotide in a test sample. The vector analysis is most conveniently carried out using growth curves having data points distributed over substantially uniform time intervals. Detailed presentations concerning the determination and use of TArc and OTArc values appear in U.S. patent application Ser. No. 11/474,698, the disclosure contained in the specification and drawings of this application being incorporated by reference herein. The essential concepts underlying the vector analysis are simply illustrated in FIGS. 3A-3B.

Determining TArc Values Using Directionally Similar Vectors

One approach for determining a TArc value employs paired sets of vectors that are directionally similar. This means that the vectors share the same direction in their x-components. Thus, vectors that are directionally similar will have x-components directed toward increasing x-values. This is distinguished from the situation characterizing directionally opposed vectors, wherein one vector is directed opposite the other in the x-component.

Figure 3A:
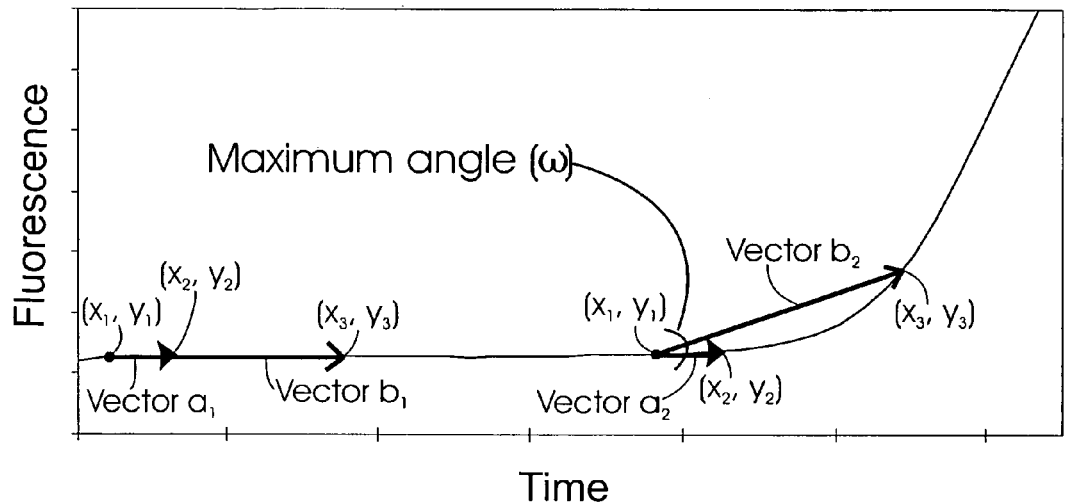
FIGS. 3A-3B graphically illustrate methods of determining TArc values using directionally similar vectors (panel A), and methods of determining OTArc values using directionally opposed vectors (panel B). Both panels show paired sets of two vectors (vectors "a" and "b") drawn on a portion of a growth curve. The angle between the two vectors is identified as ω.

FIG. 3A illustrates the arrangement of paired sets of directionally similar vectors drawn on a portion of an example growth curve. As indicated in the figure, a first vector (i.e., vector a) is established having its tail positioned on a first data point (x1,y1) of the growth curve, and its head positioned on a second data point (x2,y2) of the same growth curve. The x-component (i.e., the time or cycle number axis) of the second data point has a value greater than the x-component of the first data point (i.e., x2>x1). For the purpose of illustration, if the growth curve is parsed into 5 second intervals in the time dimension, then the time value of the first data point can be 0 seconds and the time value of the second data point can be 5 seconds. In this illustration the time values of the two data points would be spaced apart by one unit (i.e., 5 seconds) in the time dimension of the growth curve. The magnitude of the first vector would simply be the distance separating the first and second data points. The y-components of the first and second data points correspond to the magnitudes of the amplicon signals measured at the specified time points. A second vector (vector b) is established having its tail positioned on the same first data point (x1,y1) of the growth curve that was used for the first vector, and its head positioned on a third data point (x3,y3) of the growth curve having an x-component greater than the x-component of the second data point of the first vector (i.e., x3>x2). For example, if the time dimension values of the two data points used to establish the first vector are separated by one unit on the x-axis, then the two data points used to establish the second vector should be separated on the x-axis by an amount greater than this number. Indeed, the magnitude of the x-component of the second vector can be greater than the magnitude of the x-component of the first vector by at least 2 fold, and can be as high as 20 fold, or more.

In accordance with the method of determining TArc using directionally similar vectors, paired sets of two vectors (i.e., vector a and vector b), are established at regular time intervals, or cycle number intervals, along the growth curve, with each vector of a single set of paired vectors sharing a common origin (i.e., the data point corresponding to the tail of each vector). The x-components of the first and second vectors are spaced apart by predetermined values that are held constant for the analysis. For example, if the magnitude of the x-component of the first vector in each pair is 5 seconds, then the magnitude of the x-component of the second vector in each pair can be held constant at, for example, 85 seconds. This results in a plurality of paired sets of two vectors, with the origins of the different paired sets of vectors being positioned at different time points. Next, the origins of paired sets of directionally similar vectors are incremented along the time axis (i.e., the x-axis) in a reiterative process of establishing paired sets of vectors. Preferably, a plurality of the regularly spaced time points along the growth curve serve as the origins of different paired set of vectors.

Once the paired sets of vectors are established, at least one feature characterizing the relationship between two vectors of a single set is then determined. For example, the angle ($\omega$) between the two vectors can be determined using standard mathematical techniques that will be familiar to those having an ordinary level of skill in the art. The determined angle is associated with a time, or cycle number value along the growth curve. For example, the angle between two vectors (i.e., vector a and vector b) can be determined according to Equation (4).

$$\omega = \arccos[a \cdot b / (\|a\| \|b\|)] \quad \text{(Eq 4)}$$

Those having an ordinary level of skill in the art will understand from Equation (4) that the dot product of two vectors has the property defined by Equation (5), where angle omega ($\omega$) is the angle between vector a and vector b (assuming that the two vectors are non-zero, so the angle between them is well defined). The angle between the vectors has a numerical value in the interval (0, $\pi$). Since the dot product and the norms of the vectors are easily computed, one can use this formula to calculate the angle between the vectors.

$$a \cdot b = \|a\| \|b\| \cos(\omega)) \quad \text{(Eq 5)}$$

Each time value along the x-axis of the growth curve is associated with an angle value. This conveniently can be accomplished using a tabular format.

As illustrated in FIG. 3A, the angle ($\omega$) between the two directionally similar vectors reaches a maximum value within the time interval encompassing the upward concave inflection of the growth curve, and that point on the time axis is said to be the "TArc." Because the two vectors will be separated by substantial angles at the initiation and conclusion of the growth phase or log-linear phase of the growth curve, and because the time values corresponding to the first instance are of greatest interest, it is convenient, but not required to perform the vector analysis on the portion of the growth curve that precedes the conclusion of the growth phase of the growth curve. This can be accomplished, for example by using a sliding window vector analysis that excludes the portion of the curve characterized by convex curvature and the plateau phase. Determining the point at which $\omega$ is maximal over the analyzed portion of the growth curve can be accomplished simply by sorting a column of numbers, as will be familiar to those acquainted with commonly used computer spreadsheet programs, and then identifying the time point or cycle number associated with the maximum angle value in the column. It is unnecessary to calculate derivatives or slopes of curve portions to determine the maximal TArc value.

The TArc values determined in this manner can then be used for quantitative analysis of polynucleotide amounts or concentrations. More particularly, once the TArc values are established for amplification reactions conducted using known amounts of target or calibrator, those data points can be saved, plotted on a graph, or otherwise employed to establish a standard curve. Likewise, the TArc value determined for an amplification reaction performed using an unknown starting amount of analyte polynucleotide can be compared with a standard curve to determine the starting amount of analyte polynucleotide in a sample undergoing testing.

Thus, the vector-based algorithm illustrated in FIG. 3A employed paired sets of two vectors that were directionally similar in the x-dimension. This arrangement required the vectors to have different magnitudes in the x-dimension to create the opportunity for an angle therebetween as the two vectors incremented along the growth curve. The algorithm further involved identifying, as a feature of the curve, the point on the x-axis at which the smaller angle between the two vectors became maximal. When derived from analysis of reactions conducted using known quantities of an analyte polynucleotide standard, the numerical value of this feature could be plotted against the $\log_{10}$ of the input target copy number to create a standard curve. Alternatively, if the feature was derived from analysis of a reaction conducted using a test sample, the determined feature could be compared with a standard plot to determine the starting amount or concentration of analyte polynucleotide present in the test sample.

Determining OTArc Values Using Directionally Opposed Vectors

An alternative vector-based algorithm that can be used for determining OTArc values similarly involves a reiterative process of establishing paired sets of vectors along a growth curve, but employs directionally opposed vectors instead of directionally similar vectors. In contrast with the algorithm employing directionally similar vectors, the algorithm employing directionally opposed vectors does not require both of the vectors in the paired sets to have different magnitudes in the x-dimension, and involves identifying the point along the x-axis at which the angle between two vectors became minimal rather than maximal. In accordance with this latter approach, paired sets of two vectors can be established such that they are directionally opposed in the x-dimension relative to the shared origin of the two vectors. In general, one member of a pair of directionally opposed vectors extends from the shared origin in the direction of decreasing x-values, while the other member of the pair extends in the direction of increasing x-values.

Figure 3B:
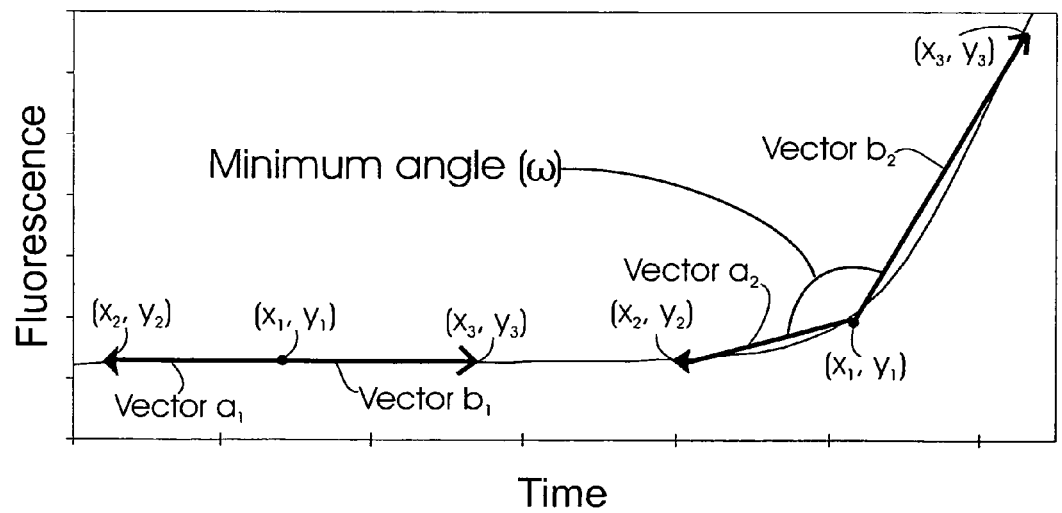

Key aspects of the algorithm which employs directionally opposed vectors, and its relationship to the algorithm which employs directionally similar vectors, can be understood with reference to FIG. 3B. This figure schematically illustrates how paired sets of directionally opposed vectors can be incremented along the x-dimension of a growth curve, and demonstrates how the angle between the two vectors becomes minimal in the vicinity of the transition between the baseline and growth phases of the growth curve. Notably, there is no requirement for the vectors to have different magnitudes of their x-components when using the algorithm based on directionally opposed vectors.

As shown in FIG. 3B, and in accordance with the algorithm employing directionally opposed vectors, a plurality of paired sets of two vectors are established at different points along the x-dimension of a growth curve. Each of the vectors of a single set of vectors shares the same origin (x1,y1). Also as indicated in the figure, the vectors are established such that their directions are opposed to each other in the x-dimension. When this is the case, the x-coordinate at the head of the first vector (i.e., vector a) has a value less than the value of the x-coordinate at shared origin, and the x-coordinate at the head of the second vector (i.e., vector b) has a value greater than the value of the x-coordinate of the shared origin. Stated differently, when using directionally opposed vectors $x2<x1<x3$, where x1 is the x-coordinate of the shared origin, where x2 is the x-coordinate at the head of the vector directed toward decreasing x-values, and where x3 is the x-coordinate at the head of the vector directed toward increasing x-values. This arrangement is distinguished from embodiments of the invention which employ directionally similar vectors, wherein $x1<x2<x3$.

Thus, if numerical data representing a growth curve for time-dependent monitoring of amplicon production in a nucleic acid amplification reaction is processed by curve fitting to result in an optimized equation, that equation can be used to parse the processed growth curve into arbitrary time intervals. For example, these time intervals could be 5 seconds each, 10 seconds each, or other desired time or cycle number interval. Continuing with this example, the magnitudes of the x-components of the directionally opposed vectors could be arbitrarily set to 50 seconds. In such a case, the origin of a first paired set of vectors could be established at x1=50 seconds, the head of the first vector would then be positioned at x2=0 seconds, and the head of the directionally opposed second vector would be positioned at x3=100 seconds. As described above, a second paired set of vectors would increment along the x-dimension of the growth curve such that the origin of the second paired set of vectors was established at x1=55 seconds, and the process repeated as desired.

The values of the y-coordinates of the vectors preferably are determined either directly from experimental data, or more preferably calculated using a moving average smoothing function, or a curve fitting operation. When curve fitting is used, values of the y-coordinates of the vectors preferably are calculated by solving optimized equations using techniques described herein, or other techniques that will be familiar to those having an ordinary level of skill in the art. With the x- and y-coordinates of the different paired sets of vectors established, the angles between the vectors can be calculated using standard mathematical approaches, such as the above-described Equation (4), and the calculated angles associated with different time points along the x-dimension of the growth curve. In accordance with the algorithm employing directionally opposed vectors, determining the time component associated with the origin of the vector pair having the minimum angle will identify the feature of the curve (i.e., the OTArc) to be plotted against the input $\log_{10}$ target copy number to create a standard curve, or to be compared with a standard curve to identify the amount or concentration of polynucleotide analyte in a test sample.

Apparatus for Implementing the Calibration Algorithm

The calibration algorithm disclosed herein is conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of a product undergoing analysis. In a highly preferred embodiment, software for executing the calibration algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

Preferably, when the computer used for executing the disclosed calibration algorithm is an integral component of an apparatus for performing and analyzing real-time nucleic acid amplification reactions, the apparatus preferably comprises a temperature-controlled incubator, a detection device for collecting signals, an analyzing device such as a computer or processor for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the disclosed calibration algorithm will be conventional components that will be familiar to those having an ordinary level of skill in the art. The temperature-controlled incubator used to perform and analyze real-time nucleic acid amplification may be of a conventional design which can hold a plurality of reaction tubes. For example, the incubator may hold up to 96 reaction samples, more preferably up to 384 reaction samples, or still more preferably up to 1536 reaction samples in a temperature-controlled block in standard amplification reaction tubes or in wells of a multi-well plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Description of the Algorithm—Creating a Parametric Calibration Curve

Creating a parametric calibration curve begins with a step for forming a plurality of standard samples, each containing a constant quantity of a nucleic acid calibrator (i.e., an internal calibrator polynucleotide), and a different known amount of an analyte polynucleotide standard. For example, each of the plurality of standard samples could contain 10,000 copies of the internal calibrator polynucleotide. The different samples could also contain known amounts of the analyte polynucleotide standard, for example, with amounts of the standard differing by 10 fold from one sample to the next.

Next, there is a step for coamplifying in a single amplification reaction the internal calibrator polynucleotide and the analyte polynucleotide standard, and measuring or otherwise determining indicia of amplification for each of the internal calibrator and analyte polynucleotide in the standard reactions. Generally speaking, these indicia preferably will be time values required for the amplification reaction to reach a certain point, or for the amount of amplicon produced to have reached a particular amount or threshold value. Such indicia may be measured in cycle numbers for amplification reactions involving thermal or other cycling, or time increments. Indicia representing time increments are preferred for isothermal amplification reactions that do not involve discrete reaction cycles requiring operator or machine intervention to promote the amplification reaction. The result of these procedures is a collection of indicia of amplification for each of the nucleic acid calibrator and analyte polynucleotide as a function of the known starting quantity of analyte polynucleotide standard that was present in the reaction mixture before the amplification reaction was initiated.

Figure 4:
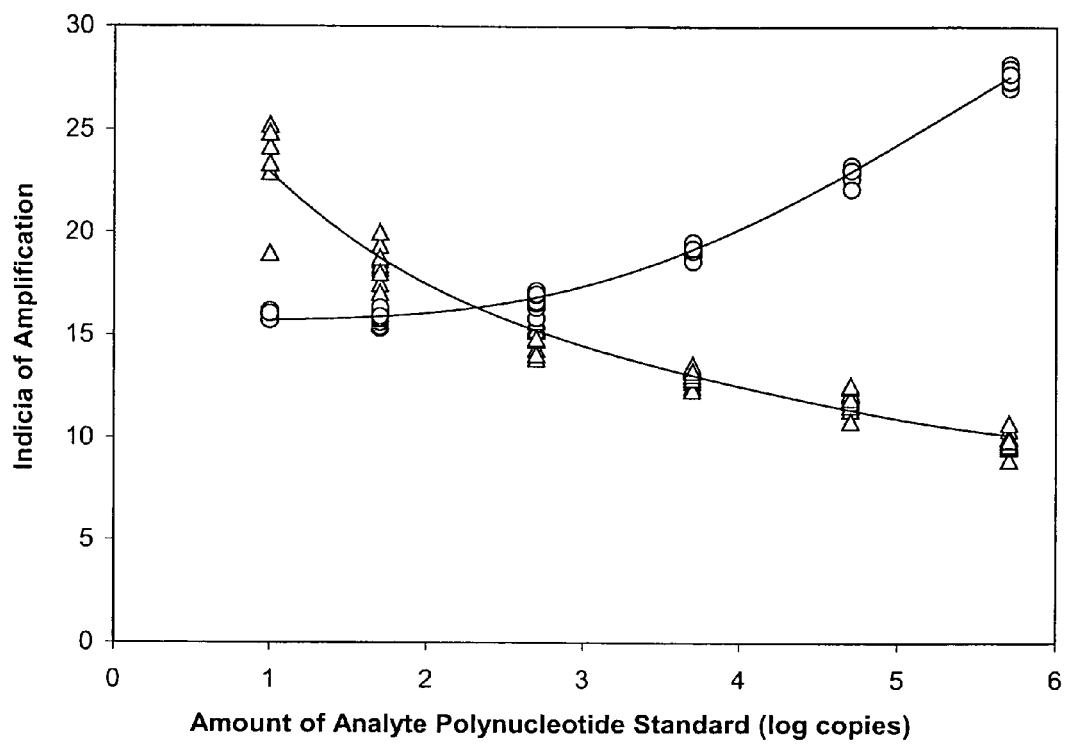
FIG. 4 is a two-dimensional graph showing indicia of amplification (y-axis) plotted against the amount of analyte polynucleotide standard (x-axis) input into a reaction mixture for real-time amplification reactions initiated with a constant quantity of nucleic acid calibrator. Data points showing results for known amounts of the analyte polynucleotide standard are depicted by open triangles (Δ), and data points showing results for the internal calibrator are depicted by open circles (○). Notably, some data points shown on the graph are overlapping. Curves drawn on the graph are the result of curve fitting parametric equations.

Of course, the resulting indicia of amplification measured for the amplified analyte polynucleotide standard and amplified internal calibrator are associated with, or related to the amount of analyte polynucleotide standard input into the reaction. This may be formalized by graphing, plotting, or more preferably electronically relating: (a) indicia of amplification for reactions conducted using known amounts of the analyte polynucleotide standard (Tt), and (b) the amount of analyte polynucleotide standard (S) input into the reaction. Likewise, this may involve graphing, plotting, or more preferably electronically relating: (a) indicia of amplification for the internal calibrator (ICt), and (b) the amount of analyte polynucleotide standard (S) input into the reaction. The individual data points in FIG. 4 represent indicia of amplification measured for the amplified analyte polynucleotide standard and amplified internal calibrator plotted as a function of the amount of analyte polynucleotide standard input into the reaction.

In accordance with the method of creating the calibration curve, the relating procedure or step involves optimizing parametric equations to fit: (1) the indicia of amplification for the amplified analyte polynucleotide standard as a function of the amount of analyte polynucleotide standard input into the reaction, and (2) the indicia of amplification for the amplified internal calibrator as a function of the amount of analyte polynucleotide standard input into the reaction. This conveniently can be accomplished by applying standard mathematical curve-fitting techniques to each of the data sets to result in equations (i.e., "fitted equations") that define curves associated therewith. Thus, equations for each of two different two-dimensional curves can be obtained by this procedure. In one embodiment, a single type of equation is used for describing each of the curves, with each of the two-dimensional curves being associated with a different set of numerical values for the equation coefficients. The parametric equation used in the curve fitting procedure preferably contains no less than three, and more preferably no less than four coefficients that are optimized or determined during the curve-fitting procedure. Highly preferred parametric equations have exactly four coefficients, while other highly preferred parametric equations have exactly five coefficients. Optimizing the parametric equation to fit the measured indicia of amplification can easily be accomplished using a commercially available software package, such as the SOLVER program which is available as an EXCEL add-in tool for finding an optimal value for a formula, and equation solving from Microsoft Corporation, (Redmond, Wash.). The curves generated by this procedure preferably are shaped such that increasing levels of the analyte polynucleotide standard input into a reaction correlate with reduced indicia of amplification for the analyte polynucleotide standard plot (e.g., the time-of-emergence is reduced), and correlate with increased indicia of amplification for the internal calibrator plot (e.g., the time-of-emergence is increased). Indeed, it is generally preferred that the value indicating the indicia of amplification for the internal calibrator is not substantially constant across the range of input analyte polynucleotide standard (S) values tested in the amplification reactions. The curves drawn in FIG. 4 represent the graphical products of fitted parametric equations solved over a range of values for the known starting amounts of input analyte polynucleotide standard (S), referred to herein as "fitted indicia of amplification." Thus, solving the fitted parametric equations at incremental values of the known starting quantity of analyte polynucleotide standard results in fitted indicia of amplification for the nucleic acid calibrator as a function of the known starting quantity of the analyte polynucleotide standard, and fitted indicia of amplification for the analyte polynucleotide standard as a function of the known starting quantity of the analyte polynucleotide standard.

Although other parametric equations have been used in the curve fitting procedure with good results, the procedures described below employed conventional four-parameter logistic ("4 PL") parametric equations having the following forms:

$$X = Tt(S) = a_x + b_x/[1+(S/c_x)^{d_x}] \quad \text{(Eq 6)}$$

$$Y = ICt(S) = a_y + b_y/[1+(S/c_y)^{d_y}] \quad \text{(Eq 7)}$$

In these equations, Tt(S) represents the indicia of amplification for a known amount of analyte polynucleotide standard as a function of the starting amount of analyte polynucleotide standard, and ICt(S) represents the indicia of amplification for the internal calibrator as a function of the starting amount of analyte polynucleotide standard. The four coefficients in these equations that can be optimized by standard procedures are identified as $a_n$-$d_n$. The number of copies of analyte polynucleotide standard input into the amplification reaction is identified by the parameter "S" in the equations. Of course, it is to be understood that success in using the method taught herein does not require the use of any particular parametric equation. For example, parametric equations based on third-order polynomials were also used with excellent results, and fall within the scope of the invention. Yet other contemplated alternatives for curve-fitting include both non-linear and linear models, including, but not limited to, regression analysis.

Next, there is a step for preparing a three-dimensional parametric calibration curve. This preferably involves establishing a relationship, such as an electronic representation of a three-dimensional curve, between: (1) indicia of amplification for the analyte polynucleotide standard (Tt); (2) indicia of amplification for the internal calibrator (ICt), and (3) the amount of analyte polynucleotide standard (S) used in the reactions yielding these indicia of amplification. In one embodiment, the result of this procedure is a standard curve plotted on a three-dimensional graph, as illustrated in FIG. 5, where the third dimension (i.e., the z axis) corresponds to the amount of analyte polynucleotide standard (S) input into the amplification reaction. Of course, such a curve will also have a projection onto the measurement plane, as illustrated in FIG. 5. Each of these related standard curves can be used for determining the amount of analyte polynucleotide present in a test sample given only the indicia of amplification measured for the coamplified analyte polynucleotide and internal calibrator.

Description of the Algorithm—Using the Calibration Curve

Steps for using a space calibration curve are now described.

First, there is a step for forming at least one test reaction mixture containing the same known starting quantity of nucleic acid calibrator polynucleotide that was present in each of the standard samples used to create the standard curve, and an unknown starting quantity of the analyte polynucleotide that is to be quantified.

Next, there is a step for coamplifying, in a single amplification reaction, the nucleic acid calibrator and any of the analyte polynucleotide that may be present in the test reaction mixture, and measuring or otherwise determining indicia of amplification for the nucleic acid calibrator and analyte polynucleotide contained in the test reaction mixture. As above, these indicia can be time values required for the amplification reaction to reach a certain point, or for the amount of amplicon produced to reach a particular amount or threshold value. Such indicia may be measured in cycle numbers for amplification reactions involving thermal or other cycling steps, or time increments. Indicia representing time increments are preferred for isothermal amplification reactions that do not involve discrete reaction cycles requiring operator or machine intervention to promote the amplification reaction.

Next, there is a step for relating, plotting or specifying (e.g., electronically specifying) in the x-y plane (i.e., the "measurement plane") of the three-dimensional parametric calibration curve the coordinates of the indicia of amplification measured for the coamplified analyte polynucleotide and internal calibrator in the test reaction. This relationship in the measurement plane of the three-dimensional calibration curve can be used for determining the amount of analyte polynucleotide contained in a test sample.

Finally, there is a step for determining the value of the parameter S that gives the minimum distance between the coordinates for the test sample in the measurement plane and the calibration curve projection in the measurement plane. Stated differently, this step involves performing calculations that vary the value of the parameter S to minimize the magnitude of the difference between the coordinates for the test sample in the measurement plane and the calibration curve projection in the measurement plane. The amount of target present in the test sample is estimated as the value of the parameter S which provides this minimum distance. This can be accomplished by using the Euclidean norm, as described above, and an iterative computing process.

Application of the Calibration Method to Quantitation of Analyte Polynucleotides The following Example demonstrated the interdependence between production of analyte amplicons and internal calibrator amplicons in a real-time nucleic acid amplification system. In this system the internal calibrator copy number was held constant, and the number of copies of the analyte polynucleotide standard was varied. While the transcription-associated amplification method employed in this illustration used the combination of one primer having a 3'-end extendable by a DNA polymerase and one T7 promoter-provider oligonucleotide having a blocked 3'-end that could not be extended by a DNA polymerase (essentially as described by Becker et al., in published U.S. patent application Ser. No. 11/213,519), the parametric calibration method described herein can also be used with essentially any other in vitro nucleic acid amplification system, including those employing paired sets of oppositely disposed primers having 3'-ends extendable by a DNA polymerase. Indeed, competitive amplification systems resulting from coamplification of analyte polynucleotide and internal calibrator using a shared set of amplification oligonucleotides or primers give excellent results with the parametric calibration method disclosed herein, and so represent a category of preferred amplification reactions. Fluorescence emission results gathered as a function of amplification reaction time were processed using a mathematical algorithm for determining the point at which the fluorescent signal exceeded a pre-determined threshold, sometimes referred to as the "time-of-emergence" above background. The nature of this processing step is not considered critical, and many alternative processing approaches can be used for determining a point on the growth curve. Examples of methods of determining time-dependent indicia of amplification include TTime, which is described in U.S. patent application Ser. No. 60/659,874 at pages 110-116, and TArc and OTArc, which are both described in U.S. patent application Ser. No. 11/474,698, and others. To illustrate the invented parametric calibration algorithm, the time-dependent fluorescence results obtained in the following Example were processed by the TTime algorithm for determining time-dependent indicia of amplification.

Example 1 describes a procedure wherein known numbers of an analyte polynucleotide standard were coamplified in a single amplification reaction with known, constant numbers of an internal calibrator polynucleotide. In this Example the analyte polynucleotide standard and the internal calibrator were amplified using different amplification oligonucleotides. An alternative arrangement wherein each of the polynucleotides amplifies using a shared set of amplification oligonucleotides in a competitive amplification format also has been used with very good results, and represents a preferred embodiment.

EXAMPLE 1

Time-Dependent Monitoring of Analyte and Internal Calibrator Amplicon Synthesis

HIV-1 subtype B and nucleic acid calibrator sequences were amplified using a transcription-associated amplification method as described in U.S. patent application Ser. No. 11/213,519. Time-dependent synthesis of HIV-1 analyte polynucleotide amplicons and internal calibrator amplicons was monitored using distinguishable molecular torch hybridization probes. In these procedures the two multiplexed amplification reactions did not share either primers or probes in common. Thus, the HIV-1 target was amplified using a T7-provider oligonucleotide, a non-T7 primer, a blocker oligonucleotide, and detected using molecular torch, where each of these was specific for the HIV-1 target and not the nucleic acid calibrator. Likewise, the internal calibrator was amplified using a T7-provider oligonucleotide, a non-T7 primer, a blocker oligonucleotide, and detected using a molecular torch, where each of these was specific for the nucleic acid calibrator and not the HIV-1 target. Amplification reactions were carried out at constant temperature (i.e., without thermal cycling), and amplicon formation was monitored by fluorescence emission as a function of time. Signals produced by the different hybridization probes were distinguishable from each other by their fluorescent emission spectra. All reactions included 30,000 copies of the internal calibrator, and were performed in replicates of twelve. The number of copies of HIV-1 target ranged from 0-500,000 copies/reaction. Amplification reactions and detection steps were carried out using a CHROMO4 REAL-TIME DETECTOR instrument (MJ Research/Bio-Rad Laboratories, Inc.; Hercules, Calif.). Time-dependent fluorescent signals proportional to the extent of amplicon synthesis were normalized to a maximum relative fluorescence unit (RFU) of one. Fluorescence readings indicating the amount of amplicon present in the reaction mixture were taken approximately every 20 seconds. TTime values indicating the time-of-emergence of the fluorescent signal above a background threshold for the different targets were determined essentially as disclosed in U.S. patent application Ser. No. 60/659,874.

Results from the amplification reactions were collected and processed using different mathematical approaches for comparison. Graphic plots of fluorescence signals against reaction time (i.e., real-time run curves) for analyte polynucleotide showed strong evidence for overlap in samples having amounts of analyte polynucleotide that differed by up to 10 fold. Thus, the run curves for reactions conducted using 10 copies of the analyte polynucleotide were somewhat interspersed with run curves for reactions conducted using 50 copies of the analyte polynucleotide, etc. This variation was quantitatively reflected by the relatively high standard deviation values appearing in Table 1. Generally speaking, reactions initiated using higher levels of the analyte polynucleotide standard characteristically suppressed internal calibrator amplicon synthesis when compared with reactions initiated using lower levels of analyte polynucleotide standard. More specifically, and as summarized in Table 1, fluorescent signals representing production of HIV-1 analyte polynucleotide amplicons yielded TTime values ranging from as short as 9.9 minutes for the highest level of target tested, to as long as 23.2 minutes for the lowest level of target tested. The TTime values determined for the internal calibrator ranged from as short as 15.43 minutes to as long as 27.59 minutes.

TABLE 1

Summarized Quantitative Results from Nucleic Acid Amplification Reactions

| | Analyte Polynucleotide Standard | | | Internal Calibrator | | |
|---|---|---|---|---|---|---|
| Input log$_{10}$ copies of analyte | # Reactions detecting analyte | Avg TTime (minutes) | Std Dev TTime (minutes) | # Reactions detecting internal calibrator | Avg TTime (minutes) | Std Dev TTime (minutes) |
| 0 | 0 | N/A | N/A | 12 | 15.43 | 0.33 |
| 1 | 6 | 23.2 | 2.26 | 12 | 15.97 | 0.46 |
| 1.7 | 12 | 17.7 | 1.51 | 12 | 15.80 | 0.30 |
| 2.7 | 12 | 15.0 | 0.62 | 12 | 16.61 | 0.37 |
| 3.7 | 12 | 13.1 | 0.38 | 12 | 19.18 | 0.29 |
| 4.7 | 12 | 11.9 | 0.50 | 12 | 22.89 | 0.33 |
| 5.7 | 12 | 9.9 | 0.45 | 12 | 27.59 | 0.32 |

The following Example illustrates how plotting time-dependent indicia of amplification as a function of the input analyte polynucleotide copy number graphically confirmed the inverse relationship between kinetic profiles for the analyte polynucleotide and internal calibrator amplification reactions. As described below, the time-dependent indicia of amplification for the HIV-1 analyte polynucleotide standard decreased as a function of increasing amounts of input analyte polynucleotide, while the time-dependent indicia of amplification for the internal calibrator continuously increased. This confirmed a strong interdependence between the amount of analyte polynucleotide present in the reaction mixture prior to the start of amplification and the time-dependent indicia of amplification for both the analyte polynucleotide and the internal calibrator. Further illustrated is a curve-fitting procedure which resulted in a set of optimized parametric equations describing fitted curves.

Example 2 illustrates the inverse relationship between amplification profiles for analyte polynucleotide and internal calibrator, as well as the use of curve-fitting techniques to obtain parametric equations fitting experimental results. A subsequent Example describes use of the obtained equations for constructing a three-dimensional calibration curve.

EXAMPLE 2

Relating Time-Dependent Indicia of Amplification to the Amounts of Analyte Polynucleotide Standard Input into Amplification Reactions Numerical values for the time-dependent indicia of amplification (i.e., TTime values) determined for the synthesis of analyte polynucleotide standard and internal calibrator amplicons obtained in the amplification reactions of the preceding Example were entered into an electronic spreadsheet and visualized in a two-dimensional graphic format having the amount of input analyte polynucleotide standard (e.g., measured in log$_{10}$ copies) on the x-axis, and time-dependent indicia of amplification for each of the amplified targets on the y-axis. Next, standard procedures familiar to those having an ordinary level of skill in the art were used to fit curves to the measured data points. This involved optimizing parametric equations to minimize deviation between a fitted curve and the measured data. Different approaches were used for establishing these relationships in a quantifiable manner, and different model parametric equations can be used in the curve-fitting procedure. The technique was particularly illustrated using a general equation expressed as a function of the parameter S, where S was the amount of input analyte polynucleotide standard. Treating the analyte polynucleotide and internal calibrator data sets separately, numerical values for $a_n$-$d_n$ in Equations 6-7 were optimized using commercially available SOLVER software which is available as an EXCEL spreadsheet software add-in tool from Microsoft Corporation (Redmond, Wash.). The results of this operation were two equations, each having a fixed set of optimized coefficients ($a_n$-$d_n$) that defined curves fitted to the measured time-dependent indicia of amplification for the analyte polynucleotide and internal calibrator, respectively. These equations had the forms:

$$X = Tt(S) = a_x + b_x / [1 + (S/c_x)^{d_x}] \quad \text{(Eq 6)}$$

$$Y = ICt(S) = a_y + b_y / [1 + (S/c_y)^{d_y}] \quad \text{(Eq 7)}$$

Two-dimensional plots of the data points representing time-dependent indicia of amplification, expressed as TTime values, as a function of the amount of input analyte polynucleotide, together with fitted curves representing solutions to the optimized parametric equations are presented in FIG. 4.

The following Example describes the establishment of a three-dimensional relationship between: (1) time-dependent indicia of amplification for the analyte polynucleotide standard (Tt); (2) time-dependent indicia of amplification for the internal calibrator (ICt), and (3) the amount of polynucleotide standard (S) used in the reactions which yielded these time-dependent indicia.

Example 3 illustrates the preparation of a three-dimensional parametric calibration curve.

EXAMPLE 3

Establishing a Parametric Calibration Curve in Three Dimensions

An electronic spreadsheet created using MATLAB software (The MathWorks; Natick, Mass.) was employed to establish a three-dimensional calibration curve using the equations defining fitted curves, as described in the previous Example. Three functions used for establishing this relationship were: (1) time-dependent indicia of amplification for the analyte polynucleotide standard as a function of the amount of analyte polynucleotide standard input into the reaction; (2) time-dependent indicia of amplification for the internal calibrator as a function of the amount of analyte polynucleotide standard input into the reaction; and (3) a mathematical function relating the amount of analyte polynucleotide standard in the z-dimension. Three axes of a graphic plot used to display the calibration curve were assigned as follows:

$$X = Tt(S) = a_x + b_x/[1+(S/c_x)^{d_x}] \quad \text{(Eq 6)}$$

$$Y = ICt(S) = a_y + b_y/[1+(S/c_y)^{d_y}] \quad \text{(Eq 7)}$$

$$Z = Z(S) = \log_{10}(S) \quad \text{(Eq 8)}$$

By varying the value of S in the z-dimension, solving for the respective values of x and y, and then graphically displaying the result there was established a three-dimensional calibration curve shown in FIG. 5. This three-dimensional curve represents the relationship between: (1) measurable indicia of amplification in reactions that coamplify variable amounts of an analyte polynucleotide and a constant amount of an internal calibrator; and (2) the amount of analyte polynucleotide standard present in the reaction mixture at the start of the amplification reaction. Because the x-y plane of the three-dimensional plot relates the measurable indicia of amplification for analyte polynucleotide and internal calibrator to each other, this plane is referred to as the "measurement plane."

method. Values determined in Example 1 for the indicia of amplification for the HIV-1 analyte polynucleotide as a function of the amount of input analyte polynucleotide in the reactions were used to establish a line of best fit by a conventional linear least squares curve fitting procedure. The average number of $\log_{10}$ copies of the HIV-1 analyte, the standard deviation of the number of $\log_{10}$ copies of HIV-1 analyte, and the average $\log_{10}$ copy difference determined from the line of best fit were calculated to assess the quality of the resulting calibration plot in the absence of any adjustment using internal calibration. Parallel determinations were made using indicia of amplification determined for both the analyte polynucleotide and internal calibrator, and the parametric calibration curves shown in FIG. 5 which relate (a) TTime values for amplification of analyte polynucleotide, (b) TTime values for amplification of internal calibrator polynucleotide, and (c) the number of copies of analyte polynucleotide input into the reactions. A summary of this information is presented in Table 2.

TABLE 2

Analyte Polynucleotide Quantitation was Improved by the Parametric Calibration Method

| | No Internal Calibration Adjustment | | | Parametric Calibration Adjustment | | |
|---|---|---|---|---|---|---|
| Input $\log_{10}$ copies of analyte | Analyte Avg $\log_{10}$ copies | Analyte Std Dev $\log_{10}$ copy | Analyte Avg $\log_{10}$ copy difference | Analyte Avg $\log_{10}$ copies | Analyte Std Dev $\log_{10}$ copy | Analyte Avg $\log_{10}$ copy difference |
| 0 | N/A | N/A | N/A | N/A | N/A | N/A |
| 1 | −1.48 | 1.20 | −2.48 | 1.00 | 0.33 | 0.00 |
| 1.7 | 1.45 | 0.80 | −0.25 | 1.94 | 0.36 | 0.25 |
| 2.7 | 2.92 | 0.33 | 0.23 | 2.73 | 0.12 | 0.04 |
| 3.7 | 3.92 | 0.20 | 0.22 | 3.69 | 0.04 | −0.01 |
| 4.7 | 4.57 | 0.27 | −0.13 | 4.65 | 0.05 | −0.05 |
| 5.7 | 5.63 | 0.24 | −0.07 | 5.71 | 0.07 | 0.01 |

Also shown in FIG. 5 is a projection of the three-dimensional calibration curve onto the two-dimensional measurement plane. The two-dimensional relationship, either in electronic spreadsheet form or graphical form, corresponding to the measurement plane in the figure can alternatively be produced by solving the fitted parametric equations for Tt(S) and ICt(S) over a range of values for the input amount of analyte polynucleotide standard (S) and then graphing or electronically representing the results. The three-dimensional standard curve and the two-dimensional curve in the measurement plane can be used for determining the amount of analyte polynucleotide present in a test sample given the time-dependent indicia of amplification measured for the coamplified analyte polynucleotide and internal calibrator.

Example 4 describes evidence that the parametric calibration method improved both the precision and accuracy of analyte polynucleotide quantitation. This conclusion was based on analysis of results obtained in the preceding Examples.

EXAMPLE 4
Parametric Calibration Method Improved Quantitation of Analyte Polynucleotides Using a Real-Time Nucleic Acid Amplification Protocol Statistical analysis of results from the above-described nucleic acid amplification reactions was used to assess improvements to precision and accuracy of calibration curves resulting from application of the parametric calibration The results presented in Table 2 confirmed that the parametric calibration method substantially improved quantitation of analyte polynucleotides using time-dependent monitoring of in vitro nucleic acid amplification reactions. Ideally, the numbers appearing in the columns marked "Analyte Std Dev $\log_{10}$ copy" should be as low as possible. The values in these columns represent the standard deviation of the calculated analyte $\log_{10}$ copy number, and so relate to assay precision. Comparing the entries in columns three and six reveals that the parametric calibration method uniformly yielded advantageously lower standard deviation, and so reflected improved assay precision. Also ideally, the numbers appearing in the columns marked "Analyte Avg $\log_{10}$ copy difference" should be as close to zero as possible. The values in these columns represent the ability to predict the analyte polynucleotide $\log_{10}$ copy number accurately. Comparing the entries in columns four and seven, it was clear that the parametric calibration method yielded improved accuracy in the quantitation at all analyte polynucleotide copy levels, except for the 50 copy entry which was essentially the same for both data processing algorithms. Overall, the information in Table 2 indicated that the parametric calibration method improved precision and accuracy of analyte polynucleotide quantitation.

The following Example describes amplification reactions that contained known amounts of analyte polynucleotide, and that were purposely inhibited to assess the value of the parametric calibration method. These procedures also involved processing time-dependent fluorescence readings using three different curve analysis algorithms. The first algorithm involved the threshold-based determination of the TTime, as described in the foregoing Examples. The second and third curve analysis algorithms involved determination of the TArc and OTArc values, neither of these determinations requiring assessment of a baseline level of fluorescence or a threshold of fluorescence used for determining indicia of amplification.

Example 5 describes comparative evidence showing that the parametric calibration method was useful for quantifying the amount of analyte polynucleotide contained in samples exhibiting inhibition of amplification. Results showed that the improvement was independent of the curve analysis algorithm used to establish the indicia of amplification.

EXAMPLE 5

Parametric Calibration Method Improves Quantitation of Analyte Polynucleotides in Test Samples Exhibiting Inhibited Nucleic Acid Amplification Three-dimensional parametric calibration curves (e.g. as shown in FIG. 5) were prepared using the procedures described in the foregoing Examples, except that the same data sets were processed in parallel to identify as indicia of amplification using different curve analysis algorithms. Amplification reactions used for preparing the parametric calibration curves were not purposely inhibited. Amplification reactions for experimental test samples were prepared to contain known amounts of the HIV-1 analyte polynucleotide in combination with 30,000 copies of the unrelated internal calibration polynucleotide. Test sample reactions were supplemented to contain 5-20% by volume of a HEPES-based wash buffer to inhibit efficiency of the subsequently performed transcription-associated amplification reaction. Amplification reactions were performed as described in the foregoing Examples, and fluorescence readings proportional to amplicon production were monitored as a function of reaction time for both analyte and internal calibrator polynucleotides. All reactions were carried out in replicates of ten. The resulting data sets were processed in parallel to identify indicia of amplification using TTime, TArc, and OTArc algorithms. Amounts of analyte polynucleotide contained in the inhibited test samples were calculated by two different methods. In the first approach, amounts of analyte polynucleotide were estimated without using internal calibration data. These determinations involved only the indicia of amplification determined for the analyte polynucleotide contained in the test sample, and a linear fit of the indicia of amplification for analyte polynucleotide standard as a function of the amount of input analyte polynucleotide standard for the standard reactions. In the second approach, amounts of analyte polynucleotide were estimated using the three-dimensional parametric calibration curves and the procedure involving minimization of the Euclidian norm separating the experimental data point plotted in the measurement plane from the projection of the three-dimensional parametric calibration curve onto the measurement plane, as described above. In all instances, the indicia of amplification were consistent, meaning that calibration data prepared using TTime values were used for assessing the amount of analyte polynucleotide in the test sample using data processed to identify TTime. Likewise, calibration data prepared using TArc and OTArc values were used for assessing the amount of analyte polynucleotide in the test sample using data processed to identify TArc and OTArc, respectively. Summarized results of these procedures are presented in Tables 3-5.

TABLE 3

Improvement to Quantitation of Analyte Polynucleotide Under Conditions of Inhibited Amplification (TTime Analysis)

| | | No Internal Calibration Adjustment | | | | | Parametric Calibration Adjustment | | | | |
|---|---|---|---|---|---|---|---|---|---|---|---|
| Input $\log_{10}$ copies analyte | % Wash buffer inhibitor | Data points used | Std Dev $\log_{10}$ copy | Avg $\log_{10}$ copy difference | Weighted Std Dev $\log_{10}$ copy | Weighted Avg $\log_{10}$ copy difference‡ | Data points used | Std Dev Adj $\log_{10}$ copy | Avg $\log_{10}$ copy difference | Weighted Std Dev $\log_{10}$ copy | Weighted Avg $\log_{10}$ copy difference‡ |
| 3.0 | 5 | 10 | 0.27 | −0.50 | 2.66 | 4.97 | 10 | 0.20 | −0.36 | 2.05 | 3.61 |
| 4.0 | 5 | 10 | 0.04 | −0.38 | 0.39 | 3.84 | 10 | 0.06 | −0.22 | 0.64 | 2.17 |
| 5.0 | 5 | 10 | 0.04 | −0.46 | 0.44 | 4.59 | 10 | 0.07 | 0.38 | 0.71 | 3.77 |
| 3.0 | 10 | 10 | 0.37 | −1.41 | 3.68 | 14.07 | 10 | 0.26 | −1.02 | 2.56 | 10.20 |
| 4.0 | 10 | 10 | 0.08 | −0.75 | 0.79 | 7.54 | 10 | 0.11 | −0.57 | 1.07 | 5.75 |
| 5.0 | 10 | 10 | 0.07 | −0.88 | 0.75 | 8.79 | 10 | 0.04 | 0.55 | 0.43 | 5.54 |
| 3.0 | 20 | 5 | 0.15 | −2.69 | 0.73 | 13.43 | 5 | 0.08 | −1.82 | 0.42 | 9.11 |
| 4.0 | 20 | 10 | 0.13 | −2.19 | 1.30 | 21.92 | 10 | 0.10 | −1.86 | 0.96 | 18.61 |
| 5.0 | 20 | 10 | 0.05 | −2.09 | 0.51 | 20.90 | 10 | 0.03 | 1.10 | 0.34 | 11.02 |

‡absolute value

TABLE 4

Improvement to Quantitation of Analyte Polynucleotide Under Conditions of Inhibited Amplification (TArc Analysis)

| | | No Internal Calibration Adjustment | | | | | Parametric Calibration Adjustment | | | | |
|---|---|---|---|---|---|---|---|---|---|---|---|
| Input $\log_{10}$ copies analyte | % Wash buffer inhibitor | Data points used | Std Dev $\log_{10}$ copy | Avg $\log_{10}$ copy difference | Weighted Std Dev $\log_{10}$ copy | Weighted Avg $\log_{10}$ copy difference‡ | Data points used | Std Dev Adj $\log_{10}$ copy | Avg $\log_{10}$ copy difference | Weighted Std Dev $\log_{10}$ copy | Weighted Avg $\log_{10}$ copy difference‡ |
| 3.0 | 5 | 10 | 0.27 | −0.52 | 2.71 | 5.22 | 10 | 0.19 | −0.21 | 1.90 | 2.09 |
| 4.0 | 5 | 10 | 0.05 | −0.50 | 0.54 | 5.01 | 10 | 0.03 | −0.39 | 0.33 | 3.90 |
| 5.0 | 5 | 10 | 0.05 | −0.51 | 0.46 | 5.05 | 10 | 0.12 | 0.19 | 1.16 | 1.87 |
| 3.0 | 10 | 10 | 0.40 | −1.50 | 4.00 | 14.96 | 10 | 0.27 | −0.77 | 2.73 | 7.69 |
| 4.0 | 10 | 10 | 0.06 | −0.89 | 0.63 | 8.95 | 10 | 0.06 | −0.56 | 0.62 | 5.63 |
| 5.0 | 10 | 10 | 0.07 | −1.00 | 0.68 | 9.99 | 10 | 0.14 | −0.03 | 1.36 | 0.25 |
| 3.0 | 20 | 5 | 0.18 | −2.91 | 0.92 | 14.56 | 5 | 0.12 | −1.42 | 0.61 | 7.09 |
| 4.0 | 20 | 10 | 0.11 | −2.50 | 1.11 | 25.01 | 10 | 0.09 | −1.40 | 0.93 | 14.01 |
| 5.0 | 20 | 10 | 0.10 | −2.32 | 1.00 | 23.23 | 10 | 0.16 | −0.47 | 1.60 | 4.70 |

‡absolute value

TABLE 5

Improvement to Quantitation of Analyte Polynucleotide Under Conditions of Inhibited Amplification (OTArc Analysis)

| | | No Internal Calibration Adjustment | | | | | Parametric Calibration Adjustment | | | | |
|---|---|---|---|---|---|---|---|---|---|---|---|
| Input $\log_{10}$ copies analyte | % Wash buffer inhibitor | Data points used | Std Dev $\log_{10}$ copy | Avg $\log_{10}$ copy difference | Weighted Std Dev $\log_{10}$ copy | Weighted Avg $\log_{10}$ copy difference‡ | Data points used | Std Dev Adj $\log_{10}$ copy | Avg $\log_{10}$ copy difference | Weighted Std Dev $\log_{10}$ copy | Weighted Avg $\log_{10}$ copy difference‡ |
| 3.0 | 5 | 10 | 0.27 | −0.52 | 2.73 | 5.22 | 10 | 0.17 | −0.17 | 1.68 | 1.72 |
| 4.0 | 5 | 10 | 0.06 | −0.50 | 0.58 | 5.01 | 10 | 0.04 | −0.41 | 0.36 | 4.07 |
| 5.0 | 5 | 10 | 0.05 | −0.51 | 0.47 | 5.05 | 10 | 0.10 | 0.14 | 1.00 | 1.41 |
| 3.0 | 10 | 10 | 0.40 | −1.50 | 4.03 | 14.96 | 10 | 0.23 | −0.61 | 2.34 | 6.14 |
| 4.0 | 10 | 10 | 0.07 | −0.89 | 0.67 | 8.95 | 10 | 0.06 | −0.54 | 0.64 | 5.39 |
| 5.0 | 10 | 10 | 0.06 | −1.00 | 0.61 | 9.99 | 10 | 0.12 | −0.09 | 1.19 | 0.91 |
| 3.0 | 20 | 5 | 0.19 | −2.91 | 0.93 | 14.56 | 5 | 0.10 | −0.98 | 0.52 | 4.91 |
| 4.0 | 20 | 10 | 0.12 | −2.50 | 1.15 | 25.01 | 10 | 0.09 | −1.13 | 0.85 | 11.31 |
| 5.0 | 20 | 10 | 0.10 | −2.32 | 1.02 | 23.23 | 10 | 0.12 | −0.48 | 1.23 | 4.79 |

‡absolute value

A normalized ranking system was used to verify the parametric calibration method improved analyte polynucleotide quantitation when amplification reactions exhibited inhibition. Additionally, this assessment allowed comparison of the relative effectiveness of different methods of determining indicia of amplification useful in conjunction with the parametric calibration method. This ranking system involved first determining the number of trials to be included in the analysis (i.e., summing the columns identified as "Data points used" in Tables 3-5). Next, the sums of the "Weighted Std Dev $\log_{10}$ copy" columns in each table were determined and then divided by the number of trials included in the analysis. This gave a weighted measure of assay precision. Next, the sums of the absolute value of the "Weighted avg $\log_{10}$ copy difference" columns in each table were determined and then divided by the number of trials included in the analysis. This gave a weighted measure of assay accuracy. The calculated weighted measures of assay precision and accuracy were multiplied, and the resulting product multiplied by 100 to obtain a single value reflecting a composite score for precision and accuracy. An ideal score in this assessment would be zero. Results of these calculations are presented in Table 6. Also presented in the table is an indicator of the magnitude of improvement due to the calibration adjustment. This value was determined by subtracting from the assay quality score for unadjusted condition the assay quality score for the adjustment by the parametric calibration method, and then dividing the difference by the assay quality score for unadjusted condition. In the example wherein the indicia of amplification were determined by the TTime algorithm, the improvement score was calculated as (15.59-8.87)/15.59. An improvement score of zero would indicate no improvement, while an ideal improvement score would be one.

TABLE 6

Parametric Calibration Method Improves Analyte Quantitation in Inhibited Samples Using Different Curve Analysis Algorithms

| | | No Adjustment | Adjustment by Parametric Calibration Method | Improvement Score |
|---|---|---|---|---|
| Run Curve Analysis Algorithm | TTime | 15.59 | 8.87 | 0.43 |
| | TArc | 18.68 | 7.34 | 0.61 |
| | OTArc | 18.89 | 5.52 | 0.71 |

The ranking information summarized in Table 6 confirmed that each of three different methods of determining indicia of amplification for the analyte polynucleotide and internal calibrator gave good results when used in conjunction with the parametric calibration method to quantify analyte polynucleotides, even when amplification reactions were substantially inhibited. The final column in Table 6 indicates the relative improvement to assay quality among the different methods of determining indicia of amplification. Entries closer to a value of 1.0 indicate increasingly better levels of improvement. As will be drawn from Table 6, the two run curve analysis algorithms (i.e., TArc and OTArc) that did not involve determining the time at which a run curve exceeded an arbitrary threshold yielded the greatest improvement. Notably, when the above analysis is limited to results from grossly inhibited samples (i.e., corresponding to reactions containing 20% wash buffer), the improvement scores resulting from use of the parametric calibration method are even more dramatic.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the appended claims.

What is claimed is:

1. A method of preparing a parametric calibration curve for quantifying an analyte polynucleotide contained in a test sample, comprising the steps of:
   forming a plurality of standard samples, each containing a constant quantity of a nucleic acid calibrator and a known starting quantity of an analyte polynucleotide standard;
   coamplifying the nucleic acid calibrator and the analyte polynucleotide standard in an in vitro nucleic acid amplification reaction for each of the plurality of standard samples;
   determining indicia of amplification for the nucleic acid calibrator and the analyte polynucleotide standard that coamplified in each in vitro nucleic acid amplification reaction of the coamplifying step, whereby there is obtained
      a collection of determined indicia of amplification for the nucleic acid calibrator as a function of the known starting quantity of the analyte polynucleotide standard, and
      a collection of determined indicia of amplification for the analyte polynucleotide standard as a function of the known starting quantity of the analyte polynucleotide standard;
   optimizing a first parametric equation to fit a first curve to the collection of determined indicia of amplification for the nucleic acid calibrator as a function of the known starting quantity of the analyte polynucleotide standard, thereby resulting in a first fitted equation;
   optimizing a second parametric equation to fit a second curve to the collection of determined indicia of amplification for the analyte polynucleotide standard as a function of the known starting quantity of the analyte polynucleotide standard, thereby resulting in a second fitted equation;
   solving the first and second fitted equations at incremental values of the known starting quantity of the analyte polynucleotide standard to result in
      fitted indicia of amplification for the nucleic acid calibrator as a function of the known starting quantity of the analyte polynucleotide standard, and
      fitted indicia of amplification for the analyte polynucleotide standard as a function of the known starting quantity of the analyte polynucleotide standard; and
   preparing a three-dimensional parametric calibration curve that comprises
      (a) fitted indicia of amplification for the analyte polynucleotide standard as a function of the known starting quantity of the analyte polynucleotide standard in a first dimension,
      (b) fitted indicia of amplification for the nucleic acid calibrator as a function of the known starting quantity of the analyte polynucleotide standard in a second dimension, and
      (c) a function of the known starting quantity of the analyte polynucleotide standard in a third dimension.

2. The method of claim 1, further comprising a step for projecting the three-dimensional parametric calibration curve onto a measurement plane defined by said first and second dimensions, whereby there is created a two-dimensional calibration curve projection in the measurement plane.

3. The method of claim 2, wherein the coamplifying step comprises amplifying the nucleic acid calibrator with a first set of amplification oligonucleotides, and amplifying the analyte polynucleotide standard with a second set of amplification oligonucleotides, said first and second sets of amplification oligonucleotides being different from each other.

4. The method of claim 2, wherein the step for determining indicia of amplification comprises determining threshold-based indicia of amplification.

5. The method of claim 2, wherein the step for determining indicia of amplification does not comprise determining threshold-based indicia of amplification.

6. The method of claim 2, wherein each of the first and second fitted equations has four coefficients.

7. The method of claim 1, wherein the in vitro nucleic acid amplification reaction in the coamplifying step is an isothermal in vitro nucleic acid amplification reaction.

8. The method of claim 7, wherein the isothermal in vitro nucleic acid amplification reaction is a transcription-associated amplification reaction.

9. The method of claim 2, further comprising
   forming a test reaction mixture comprising said test sample and said constant quantity of the nucleic acid calibrator;
   coamplifying in an in vitro nucleic acid test amplification reaction the nucleic acid calibrator and any analyte polynucleotide contained in the test reaction mixture; and
   determining indicia of amplification for the nucleic acid calibrator and the analyte polynucleotide that coamplified in the in vitro nucleic acid test amplification reaction.

10. The method of claim 9, further comprising quantifying the analyte polynucleotide contained in the test sample.

11. The method of claim 10, wherein the quantifying step comprises comparing the determined indicia of amplification for the nucleic acid calibrator and the analyte polynucleotide that coamplified in the in vitro nucleic acid test amplification reaction with the two-dimensional calibration curve projection in the measurement plane.

12. The method of claim 10, wherein the quantifying step comprises
   specifying in the measurement plane a test sample data point comprising coordinates for the determined indicia of amplification for the nucleic acid calibrator and the analyte polynucleotide that coamplified in the in vitro nucleic acid test amplification reaction, and
   determining a value for a third dimension coordinate of the three-dimensional parametric calibration curve that minimizes the distance separating the test sample data point and a point on the two-dimensional calibration curve projection in the measurement plane.

13. The method of claim 12, wherein the step of determining the value for the third dimension coordinate of the three-dimensional parametric calibration curve comprises calculating the length of a right triangle hypotenuse.

14. The method of claim 12, wherein the coamplifying step comprises amplifying the nucleic acid calibrator with a first set of amplification oligonucleotides, and amplifying the analyte polynucleotide standard with a second set of amplification oligonucleotides, said first and second sets of amplification oligonucleotides being different from each other.

15. The method of claim 12, wherein the step of determining indicia of amplification comprises determining threshold-based indicia of amplification.

16. The method of claim 12, wherein the step of determining indicia of amplification does not comprise determining threshold-based indicia of amplification.

17. The method of claim 12, wherein each of the first and second fitted equations comprises four coefficients.

18. The method of claim 12, wherein the in vitro nucleic acid amplification reaction in the coamplifying step is an isothermal in vitro nucleic acid amplification reaction.

19. The method of claim 12, wherein the isothermal in vitro nucleic acid amplification reaction is a transcription-associated amplification reaction.

20. A method of quantifying an analyte nucleic acid contained in a test sample by internal calibration adjustment of nucleic acid amplification results, said method comprising the steps of:
(a) collecting a standard data set and a test data set,
said standard data set comprising results from a plurality of standard nucleic acid amplification reactions, each standard nucleic acid amplification reaction comprising a constant starting quantity of a nucleic acid calibrator and a different known starting quantity of an analyte polynucleotide standard, said plurality of standard nucleic acid amplification reactions yielding indicia of amplification for the analyte polynucleotide standard as a function of the known starting quantity of the analyte polynucleotide standard, and
indicia of amplification for the nucleic acid calibrator that coamplified with the analyte polynucleotide standard as a function of the known starting quantity of the analyte polynucleotide standard,
said test data set comprising results from a test nucleic acid amplification reaction comprising said constant starting quantity of the nucleic acid calibrator and an unknown starting quantity of the analyte nucleic acid, said test nucleic acid amplification reaction yielding an indicium of amplification for the analyte nucleic acid contained in the test sample, and
an indicium of amplification for the nucleic acid calibrator that coamplified with the analyte nucleic acid;
(b) preparing a three-dimensional parametric calibration curve that comprises
a first dimension comprising solutions to a first optimized parametric equation that expresses indicia of amplification for the analyte polynucleotide standard as a function of the known starting quantity of the analyte polynucleotide standard,
a second dimension comprising solutions to a second optimized parametric equation that expresses indicia of amplification for the nucleic acid calibrator as a function of the known starting quantity of analyte polynucleotide standard, and
a third dimension parameter of the first and second optimized parametric equations, said third dimension parameter comprising the known starting quantity of analyte polynucleotide standard used in said plurality of standard nucleic acid amplification reactions,
wherein the first and second dimensions of the three-dimensional parametric calibration curve define a measurement plane, and
wherein the measurement plane comprises a projection of the three-dimensional parametric calibration curve;
(c) specifying a test sample data point in the measurement plane, said test sample data point comprising a set of coordinates for the indicium of amplification for the analyte nucleic acid and the indicium of amplification for the nucleic acid calibrator that coamplified with the analyte nucleic acid in the test nucleic acid amplification reaction; and
(d) determining the minimum distance between the test sample data point specified in the measurement plane and the projection of the three-dimensional parametric calibration curve in the measurement plane by varying the value of the third dimension parameter, whereby the value of the third dimension parameter which results in the determined minimum distance estimates the quantity of the analyte nucleic acid contained in the test sample,
wherein said plurality of standard nucleic acid amplification reactions and said test nucleic acid amplification reaction are carried out with an apparatus that amplifies nucleic acids and performs time-dependent monitoring of amplicon production,
wherein said standard data set and said test data set of step (a) are collected from results produced by said apparatus, and
wherein steps (b)-(d) are implemented by a computer that receives said standard data set and said test data set.

21. The method of claim 20, wherein the determining step comprises determining by an iterative computing process.

22. The method of claim 21, wherein the iterative computing process comprises calculating the hypotenuse length for a plurality of right triangles.

23. The method of claim 22, wherein the plurality of standard nucleic acid amplification reactions and the test nucleic acid amplification reaction are isothermal amplification reactions that do not use thermal cycling to synthesize amplicons.

24. The method of claim 22, wherein said plurality of standard nucleic acid amplification reactions and the test nucleic acid amplification reaction amplify the analyte nucleic acid and analyte polynucleotide standard with a first set of two amplification oligonucleotides, and amplify the nucleic acid calibrator with a second set of two amplification oligonucleotides, and wherein said first and second sets of amplification oligonucleotides are identical to each other.

25. The method of claim 22, wherein said plurality of standard nucleic acid amplification reactions and the test nucleic acid amplification reaction amplify the analyte nucleic acid and analyte polynucleotide standard with a first set of two amplification oligonucleotides, and amplify the nucleic acid calibrator with a second set of two amplification oligonucleotides, and wherein said first and second sets of amplification oligonucleotides are not identical to each other.

26. The method of claim 22, wherein the collecting step, the preparing step, the specifying step, and the determining step are each automated by computer software that is an integral component of a device that performs the test nucleic acid amplification reaction and the plurality of standard nucleic acid amplification reactions.

27. The method of claim 20, wherein each of said plurality of standard nucleic acid amplification reactions and the test nucleic acid amplification reaction are isothermal amplification reactions that do not use thermal cycling to synthesize amplicons.

28. The method of claim 20, wherein said plurality of standard nucleic acid amplification reactions and the test nucleic acid amplification reaction amplify the analyte nucleic acid and analyte polynucleotide standard with a first set of two amplification oligonucleotides, and amplify the nucleic acid calibrator with a second set of two amplification oligonucleotides, and wherein said first and second sets of amplification oligonucleotides are identical to each other.

29. The method of claim 20, wherein said plurality of standard nucleic acid amplification reactions and the test nucleic acid amplification reaction amplify the analyte nucleic acid and analyte polynucleotide standard with a first set of two amplification oligonucleotides, and amplify the nucleic acid calibrator with a second set of two amplification oligonucleotides, and wherein said first and second sets of amplification oligonucleotides are not identical to each other.

30. The method of claim 20, wherein the first and second optimized parametric equations each comprise four fixed coefficients.

31. A system for quantifying an initial amount of an analyte polynucleotide contained in a test sample, comprising:
    an apparatus that amplifies nucleic acids and performs time-dependent monitoring of amplicon production, said apparatus being capable of generating
        a standard data set of time-dependent indicia of amplification for each of an analyte polynucleotide standard and a nucleic acid calibrator that coamplified therewith in a plurality of in vitro nucleic acid standard amplification reactions comprising a range of starting amounts of analyte polynucleotide standard and a constant starting amount of nucleic acid calibrator, and
        a test data set of time-dependent indicia of amplification for each of the analyte polynucleotide contained in the test sample and a nucleic acid calibrator that coamplified therewith in an in vitro nucleic acid test amplification reaction;
    a computer that processes the standard data set and the test data set by comparing the test data set with a three-dimensional calibration curve prepared from the standard data set, said three-dimensional calibration curve comprising
        a first dimension comprising solutions to a first optimized parametric equation that expresses indicia of amplification for analyte polynucleotide standard as a function of the known starting quantities of analyte polynucleotide standard input into the in vitro nucleic acid standard amplification reactions,
        a second dimension comprising solutions to a second optimized parametric equation that expresses indicia of amplification for coamplified nucleic acid calibrator as a function of the known starting quantities of analyte polynucleotide standard input into the in vitro nucleic acid standard amplification reactions, and
        a third dimension parameter of the first and second optimized parametric equations, said third dimension parameter comprising the known starting quantities of analyte polynucleotide standard input into the in vitro nucleic acid standard amplification reactions,
            wherein the first and second dimensions of the three-dimensional parametric calibration curve define a measurement plane, and
            wherein the measurement plane comprises a projection of the three-dimensional parametric calibration curve; and
    an output device that displays a result obtained from the processed test data set that quantifies the initial amount of analyte polynucleotide contained in the test sample.

32. The method of claim 20, wherein said computer is operably linked to said apparatus.

33. The method of claim 32, wherein said computer is an integral component of said apparatus.

* * * * *